Figure 2:
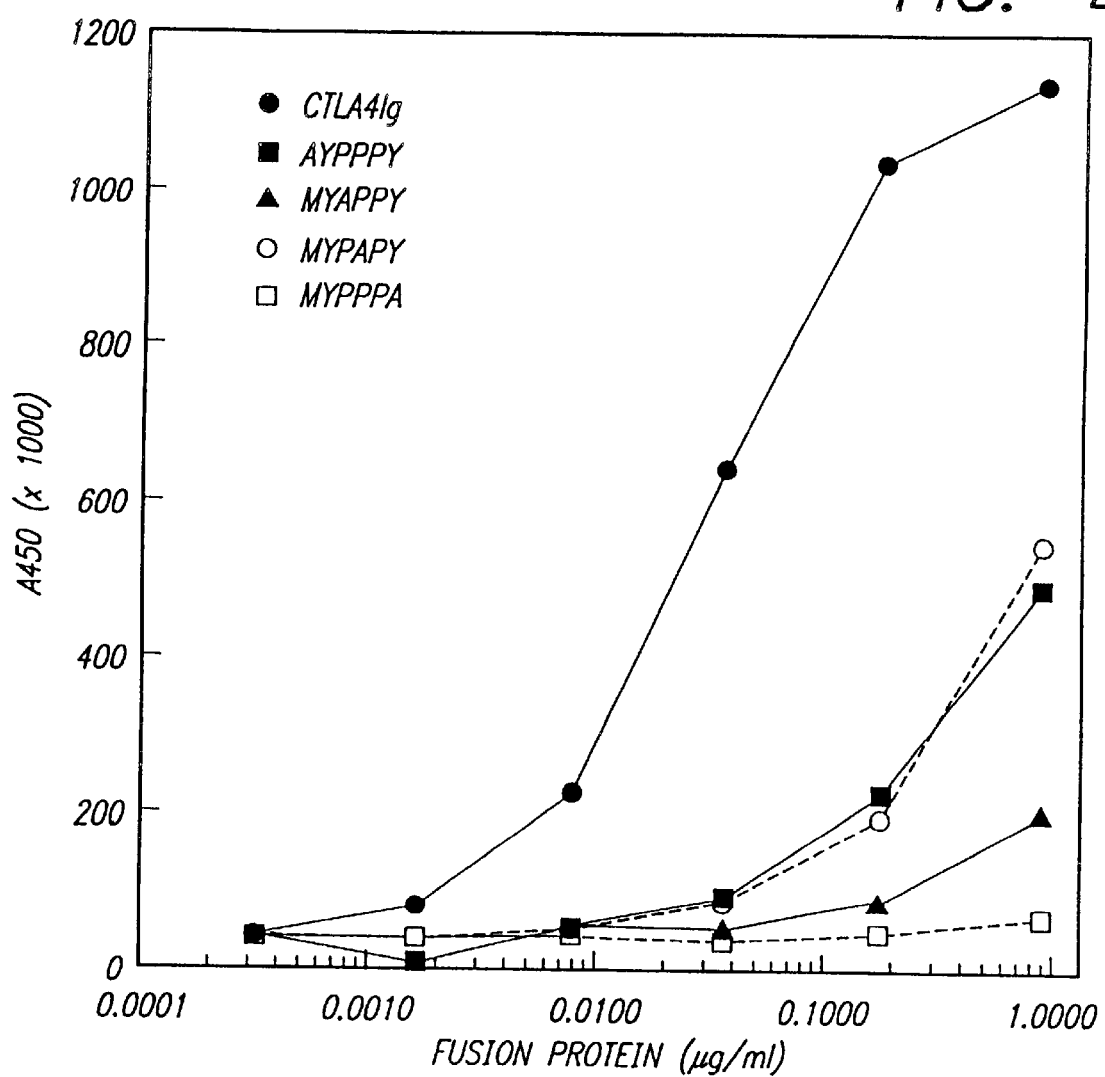

United States Patent [19]
Linsley et al.

[11] Patent Number: 5,773,253
[45] Date of Patent: Jun. 30, 1998

[54] MYPPPY VARIANTS OF CTLA4 AND USES THEREOF

[75] Inventors: Peter S. Linsley; Jeffrey A. Ledbetter, both of Seattle; Robert Peach, Edmonds, all of Wash.

[73] Assignee: Bristol-Myers Squibb Company, Princeton, N.J.

[21] Appl. No.: 505,058

[22] Filed: Jul. 21, 1995

Related U.S. Application Data

[63] Continuation-in-part of Ser. No. 228,208, Apr. 15, 1994, which is a continuation-in-part of Ser. No. 8,898, Jan. 22, 1993.

[51] Int. Cl.$^6$ .................................................. C12N 15/12
[52] U.S. Cl. .................. 435/69.7; 435/69.1; 435/172.1; 435/252.3; 435/320.1; 435/192.1; 435/358; 435/361; 435/362; 530/350; 530/387.1; 530/387.3; 530/388.75; 536/23.5
[58] Field of Search ............................. 530/350, 388.75, 530/387.1, 387.3; 536/23.5; 514/2, 8, 12, 252.3; 435/320.1, 172.1, 325, 326, 328, 332, 69.1, 69.7, 358, 361, 362; 424/192.1

[56] References Cited

U.S. PATENT DOCUMENTS

| | | | |
|---|---|---|---|
| 4,399,216 | 8/1983 | Axel ............................................. | 435/6 |
| 4,683,195 | 7/1987 | Mullis et al. ................................ | 435/6 |
| 4,683,202 | 7/1987 | Mullis ........................................ | 435/91 |
| 4,853,332 | 8/1989 | Mark et al. .......................... | 435/252.33 |

FOREIGN PATENT DOCUMENTS

| | | |
|---|---|---|
| 0 613 944 A2 | 9/1994 | European Pat. Off. . |
| 90/05541 | 5/1990 | WIPO . |
| WO 93/00431 | 1/1993 | WIPO . |
| 94/28912 | 12/1994 | WIPO . |

OTHER PUBLICATIONS

Dariavach et al., Eur.J.Immunol. 18:1901–1905, 1988.
Aruffo et al, Proc.Natl.Acad.Sci. USA 84:8573–8577, 1987.
Linsley et al., "Immunosuppression in Vivo by a Soluble Form of the CTLA–4 T Cell Activation Molecule" *Science* 257:792–795 (1992).
Lenschow et al. "Long–Term Survival of Xenogeneic Pancreatic Islet Grafts Induced by CTLA4Ig", *Science* 257:789–792 (1992).
Peach et al., "Complementarity Determining Region 1 (CDR1)–and CDR3–analogous Regions in CTLA–4 and CD28 Determine the Binding to B7–1", *J. Ex. Med.*, 180:2049–2058 (1994).
Janeway, "Approaching the Asympote? Evolution and Revolution in Immunology", *Cold Spring Harbor Symp. Quant. Biol.* LIV:1–13 (1989).
Shaw and Shimuzu, "Two Molecular Pathways of Human T Cell Adhersion; Establishment of Receptor–Ligand Relationship ", *Current Opinion in Immunology*, Eds. Kindt and Long, 1:92–97 (1988).
Hemler, "Adhesive Protein receptors on Hematopoietic Cells", *Immunology Today* 9:109–113 (1988).

Kakiuchi et al., B Cells as Antigen–Presenting Cells: The Requirement for B Cell Activation:, *J. Immunol.* 131:109–114 (1983).
Krieger et al., Antigen Presentation by Splenic B Cells: Resting B Cells are Ineffective, Whereas Activated B Cells are Effective Accessory Cells for T Cell Responses:, *J. Immunol.* 135:2937–2945 (1985).
McKenzie "Alloantigen Presentation by B Cells—Requirement for IL–1 and IL–6", *J. Immunol.* 141:2907–2911 (1988).
Hawrylowicz and Unanue, "Regulation of Antigen–Presentation–I IFN–γ Induces Antigen–Presenting Properties on B Cells", *J. Immunol.* 141:4083–4988 (1988).
Springer et al., "The Lymphocyte Function–Associated LFA–1, CD2, and LFA–3 Molecules: Cell Adhesion Receptors of the Immune System", *A Rev. Immunol.* 5:223–252 (1987).
Dinarello and Mier, Current Concepts—Lymphokines:, *New Engl. Jour. Med.* 317:940–945 (1987).
Weiss et al., "The Role of the T3/Antigen Receptor Complex in T–Cell Activation", *Ann. Rev. Immunol.* 4:593–619 (1986).
McMichael, Ed., "Non–lineage, LFA–1 Family, and Leucocyte Common Antigens: New and Previously Defined Clusters", Leukocyte Typing III, Oxford Univ. Press, Oxford UK (1987).
Moingeon et al., "CD2–mediated Adhesion Facilitates T Lymphocyte Antigen Recognition Function", *Nature* 339:312–314 (1988).
Makgoba et al., ICAM–1 A Ligand for LFA–1–Dependent Adhesion of B, T and Myeloid Cells, *Nature* 331:86–88 (1988).
Staunton et al., "Functional Clonging of ICAM–2, A Cell Adhesion Ligand for LFA–1 Homologous to ICAM–1", *Nature* 339:61–64 (1989).
Norment et al., "Cell–Cell Adhesion Mediated by CD8 and MHC Class I Molecules", *Nature* 336:79–81 (1988).
Doyle and Strominger, "Interaction Between CD4 and Class II MHC Molecules Mediates Cell Adhesion", *Nature* 330:256–259 (1987).
Stoolman, "Adhesion Molecules Controlling Lymphocyte Migration", *Cell* 56:907–910 (1989).
Brescher and Cohn, "A Theory of Self–Nonself Discrimination", *Science* 169:1042–1049 (1970).
Freeman et al., "B7, A New Member of the Ig Superfamily with Unique Expression on Activated and Neoplastic B Cells", *J. Immunol.* 143(8):2714–2722 (1989).

(List continued on next page.)

*Primary Examiner*—Lorraine M. Spector
*Assistant Examiner*—Eliane Lazar-Wesley
*Attorney, Agent, or Firm*—Mandel & Adriano

[57] ABSTRACT

The invention provides CTLA4 mutant molecules as ligands for the B7 antigen. Methods are provided for expressing CTLA4 mutant molecules as soluble, functional molecules, for preparing CTLA4 mutant fusion proteins, and for using these soluble molecules to regulate T cell interactions and immune responses mediated by such interactions.

17 Claims, 9 Drawing Sheets

OTHER PUBLICATIONS

Freedman et al., "B7, A B Cell–Restricted Antigen that Identifies Preactivated B Cells", *J. Immunol.* 138:3260–3267 (1987).

Clark et al., "Polypeptides on Human B Lymphocytes Associated with Cell Activation", *Human Immunol.* 16:100–113 (1986).

Yokochi et al., B Lymphoblast Antigen (BB–1) Expressed on Epstein–Barr Virus–Activated B Cells Blasts, B Lymphoblastoid Cell Lines, and Burkitt's Lymphomas:, *J. Immunol.* 128:823–827 (1981).

Weiss, "Structure and Function of the T Cell Antigen Receptor", *J. Clin. Invest.* 86:1015–1022 (1990).

Allen, "Antigen Processing at the Molecular Level", *Immunol. Today* 8:270–273 (1987).

Schwartz, "A Cell Culture Model for T Lymphocyte Clonal Anergy", *Science* 248:1349–1356 (1990).

Weaver and Unanue, "The Costimulatory Function of Antigen–Presenting Cells", *Immunol. Today* 11:49–55 (1990).

Aruffo and Seed, "Molecular Cloning of a CD28 cDNA by a high–Efficiency COS Cell Expression System", *Proc. Natl. Acad. Sci.* 84:8573–8577 (1987).

Damle et al., Alloantigen –Specific Cytotoxic and Suppressor T Lymphocytes are Drived from Phenotypically Distinct Precursors:, *J. Immunol.* 131:2296–2300 (1983).

June et al., "T–Cell Proliferation Involving the CD28 Pathway is Associated with Cyclosporine–Resistant Interleukin 2 Gene Expression", *Mol. Cell. Biol.* 7:4472–4481 (1987).

Thompson et al., "CD28 Activation Pathway Regulates the Production of Multiple T–Cell–Derived Lymphokines/Cytokines", *Proc. Natl. Acad. Sci.* 86:1333–1337 (1989).

Lindsten et al., "Regulation of Lymphokine Messenger RNA Stability by a Surface–Mediated T Cell Activation Pathway", *Science* 244:339–343 (1989).

Damle et al., "Monoclonal Antibody Analysis of Human T Lymphocyte Subpopulations Exhibiting Autologous Mixed Lymphocyte Reaction", *Proc. Natl. Acad. Sci.* 78:5096–5098 (1981).

Lesslauer et al., "T90/44 (9.3 Antigen). A Cell Surface Molecule with a Function in Human T Cell Activation", *Eur. J. Immunol.* 16:1289–1296 (1986).

Linsley et al., "T–Cell Antigen CD28 Mediates Adhesion with B Cells by Interacting with Activation Antigen B7/BB–1", *Proc. Natl. Acad. Sci. USA* 87:5031–5035 (1990).

Linsley et al., "Binding of the B Cell Activation Antigen B7 to CD28 Costimulates T Cell Proliferation and Interleukin 2 mRNA Accumulation", *J. Exp. Med.* 173–721–730 (1991).

Kohno et al., "CD28 Molecule as a Receptor–like Function for Accessory Signals in Cell–Mediated Augmentation of IL–2 Production", *Cell. Immunol.* 131:1–10 (1990).

Brunet et al., "A New Member of the Immunoglobulin Superfamily—CTLA–4", *Nature* 328:267–270 (1987).

Brunet et al., "A Differential Molecular Biology Search for Genes Preferentially Expressed in Functional T Lymphocytes: The CTLA Genes", *Immunol. Rev.* 103:21–36 (1988).

Dariavach et al., "Human IG Superfamily CTLA–4 Gene: Chromosomal Localizaiton and Identity of Protein Sequence Between Murine and Human CTLA–4 Cytoplasmic Domains", *Eur. J. Immunol.* 18:1901–1905 (1988).

Lafage–Pochitaloff et al., "Human CD28 and CTLA–4 and Ig Superfamily genes are Located on Chromosome 2 at bands q33–q34", *Immunogenetics* 31:198–201 (1990).

Capon et al., "Designing CD4 Immunoadhesions for AIDS Therapy", *Nature* 337:525–531 (1989).

Malik et al, "Molecular Cloning, Sequence Analysis, and Functional Expression of a Novel Growth Regulator, Oncostatin M", *Molec. and Cell. Biol.* 9:2847–2853 (1989).

Storb, "Marrow Transplantation for Severe Aplastic Anemia: Methotrexate Alone Compared wtih a Combination of Methotrexate and Cyclosporine for Prevention of Acute Graft–Versus–Host Disease", *Blood* 56:119–125 (1986).

Storb and Thomas, "Graft–Versus–Host Disease in Dog and Man: The Seattle Experience", *Immunol. Rev.* 88:215–238 (1985).

Aruffo et al., "CD44 is the Principal Cell Surface Receptor for Hyaluronate", *Cell* 61:1303–1313 (1990).

Seed and Aruffo, "Molecular Clonging of the CD2 Antigen, the T–Cell Erythrocyte Receptor, by a Rapid Immunoselection Procedure", *Proc. Natl. Acad. Sci.* 84:3365–3369 (1987).

Aruffo and Seed, "Molecular Cloning of Two CD7 (T–Cell Leukemia Antigen) cDNAs by a COS Cell Expression System", *EMBO Hour.* 6:3313–3316 (1987).

Ledbetter et al., "Crosslinking of Surface Antigens Causes Mobilization of Intracellular Ionized Calcium in T Lymphocytes", *Proc. Natl. Acad. Sci.* 84:1384–1388 (1987).

Ledbetter et al., "CD28 Ligation in T–Cell Activation: Evidence for Two Signal Transduction Pathways", *Blood* 75:1531–1539 (1990).

Damle et al., "Immunoregulatory T Lymphocytes in Man", *J. Immunol.* 139:1501–1508 (1987).

Wysocki and Sato, "Panning for Lymphocytes: A Method for Cell Selection", *Proc. Natl. Acad. Sci.* 75:2844–2848 (1978).

Damle et al., "Differential Regulatory Signals Delivered by Antibody Binding to the CD28 (Tp44) Molecule During the Activation of Human T Lymphocytes", *J. Immunol.* 140:1753–1761 (1988).

Schneck et al., "Inhibition of an Allospecific T Cell Hybridoma by Soluble Class I Proteins and Peptides; Estimation of the Affinity of a T Cell Receptor for MHC", *Cell* 56:47–55 (1989).

Recny et al., "Structural and Functional Characterization of the CD2 Immunoadhesion Domain", *J. Biol. Chem.* 265:8542–8549 (1990).

Clayton et al., "Identification of Human CD4 Residues Affecting Class II MHC Versis HIV–1 gp120 Binding", *Nature* 339:548–551 (1989).

Alzari et al., "Three–Dimensional Structure of Antibodies", *Ann. Rev. Immunol.* 6:555–580 (1988).

Hautanen et al., "Effects of Modifications of the RGD Sequence and Its Context on Recognition by the Fibronectin Receptor", *J. Biol. Chem.* 264:1437–1442 (1989).

DiMinno et al., "Exposure of Platelet Fibrinogen–Binding Sites by Collagen, Arachidonic Acid, and ADP: Inhibition by a Monoclonal Antibody to the Glycoprotein IIb–IIIa Complex", *Blood* 61:140–148 (1983).

Thiagarajan and Kelley, "Exposure of Binding Sites for Vitronectin on Platelets Following Stimulation", *J. Biol. Chem.* 263:3035–3038 (1988).

June et al., "Role of the CD28 Receptor in T–Cell Activation", *Immunology Today* 11:211–2316 (1989).

MYPPPY VARIANTS OF CTLA4 AND USES THEREOF

This application is a continuation-in-part of U.S. Ser. No. 08/228,208, filed Apr. 15, 1994 which is a continuation-in-part of U.S. Ser. No. 08/008,898, filed Jan. 22, 1993, the contents of which is incorporated by reference into the present application.

Throughout this application various publications are referenced. The disclosures of these publications in their entireties are hereby incorporated by reference into this application in order to more fully describe the state of the art to which this invention pertains.

The present invention relates to expression of CTLA4 mutant molecules and to methods for regulating cellular interactions using the CTLA4 mutant molecules.

BACKGROUND OF THE INVENTION

Central events leading to a specific immune response to antigen involve the intimate association of T lymphocytes with antigen presenting cells (APC). In order for T-cells to successfully mount cell-mediated or antibody-mediated immune responses to an antigenic stimulus, distinct activation signals are required from the APC. An antigen-specific signal occurs when the T-cell antigen receptor binds to antigenic peptides presented by major histocompatibility complex (MHC) molecules on the surface of APC's. However, this event alone is not sufficient to stimulate T-cells to proliferate and, by itself, can lead to clonal inactivation or anergy (Schwartz, R. H. (1990) *Science* 248:1349–1356). For an effective immune response to occur, a second non-antigen-specific co-stimulatory signal must also be delivered to the T-cell from an APC (Freeman et al. (*J. Immunol.* 143(8):2714–2722 (1989)).

CTLA4 is a T-cell surface receptor that associates with the B7 counter receptor, namely, B7-1 (CD80) and B7-2 (CD86), expressed on antigen-presenting cells (Hathcock et al. "Comparative Analysis of B7-1 and B7-2 Co-Stimulatory Ligands: Expression and Function" 1994 *Journal of Experimental Medicine*, 180(2):631–40). This association establishes the molecular basis for an important T-cell co-stimulatory pathway, the primary function of which is to induce T-cell cytokine production and proliferation following exposure to antigen (Linsley et al., *J. Exp. Med.* 173:721–730 (1991)). Confirmatory data has shown that one embodiment of CTLA4, namely, CTLA4Ig, is a potent inhibitor of in vitro immune responses by blocking CD28/B7 interactions, thereby preventing T-cell proliferation and inducing antigen-specific unresponsiveness (Blazar et al. "In Vivo Blockade of CD28/CTLA4: B7/BB1 Interaction With CTLA4-Ig Reduces Lethal Murine Graft-Versus-Host Disease Across the Major Histocompatibility Complex Barrier in Mice" *Blood*, 1994 Jun. 15, 83(12):3815–25).

The nature of these co-stimulatory signals has been the focus of intense research efforts, the goals of which have been not only to understand the immune system, but also to develop therapeutic agents which could block the delivery of co-stimulatory signals thereby further manipulating immune responses. The CTLA4 mutant molecules of the invention have been developed to meet these goals.

SUMMARY OF THE INVENTION

The present invention discloses CTLA4 molecules which have been mutated in order to influence their ability to bind the B7 ligands. These mutations are localized to the extracellular domain of CTLA4. Specifically, the mutations are generated at the position of the first tyrosine moiety within the MYPPPY (SEQ ID NO 11) motif of the extracellular domain of CTLA4. We show that the mutants (i.e., those having any one of alanine, arginine, asparagine, aspartic acid, cysteine, glutamine, glutamic acid, glycine, histidine, isoleucine, leucine, lysine, methionine, phenylalanine, proline, serine, threonine, tryptophan, or valine at this position) have the ability to bind B7-1 (CD80). However, some do not bind B7-2 (CD86).

Additionally provided are methods for making and using the CTLA4 mutant molecules of the invention.

BRIEF DESCRIPTION OF THE FIGURES

FIG. 1 is a graph showing the sequencing alignment of CD28 and CTLA4 family members. Sequences of human (H), mouse (M), rat (R), and chicken (Ch) CD28 are aligned with human and mouse CTLA4. Residues are numbered from the mature protein N-terminus with the signal peptides and transmembrane domains underlined and the CDR-analogous regions noted. Dark shaded areas highlight complete conservation of residues while light shaded areas highlight conservative amino acid substitutions in all family members (SEQ ID NOS 1–6).

FIG. 2 is a line graph showing CTLA4Ig and CD28Ig mutants bind B7-1.

FIG. 3 is a schematic map of CTLA4/CD28Ig hybrid fusion proteins. Open areas represent CD28 sequence; filled areas represent CTLA4 sequence; cross-hatched areas represent beginning of IgG Fc (also refer to Table I).

FIG. 4 is a line graph showing that CTLA4/CD28Ig hybrid fusion proteins bind with high avidity to B7-1 CHO cells.

FIG. 5 is a line graph showing that CTLA4/CD28Ig hybrid fusion proteins bind with high avidity to B7-1 CHO cells.

FIG. 6 is a molecular model of monomeric CTLA4Ig v-like extracellular domain.

FIG. 7 is a bar graph comparison of the ability of CTLA4Ig wild type (w.t.) and mutant molecules to bind CHO cells expressing either CD80 or CD86. The wild type molecule is designated by MYPPPY (SEQ ID NO 11), the sequence of the naturally occurring motif. The individual mutants are denoted in the same manner. The letter symbol of the amino acid substituted at the second position in this hexapeptide indicates the specific mutation.

FIG. 8 is a comparison of wild type (w.t.) and mutant binding ability using different concentrations of these CTLA4Ig fusion proteins. As disclosed in FIG. 7, the mutants are indicated by their respective motif sequences.

FIG. 9 is an antibody competition study with the LCL 816 cell line. This figure compares CTLA4Ig wild type and mutant protein binding to CD80 or CD86 in the presence of different concentrations of anti-CD80 or anti-CD86 antibody. As disclosed in FIG. 7, the specific proteins are indicated by their respective motif sequences.

DETAILED DESCRIPTION OF THE INVENTION

Definition

As used in this application, the following words or phrases have the meanings specified.

As used herein "blocking B7 interaction" means to interfere with the binding of the B7 antigens to their ligands such as CD28 and/or CTLA4 thereby obstructing T cell and B cell interaction.

As used herein a "B7-binding molecule" means any molecule which will bind any one or both of the B7 antigens.

As used herein a "molecule reactive with the CD80 antigen" means any molecule which will recognize and bind CD80.

As used herein a "molecule reactive with the CD86 antigen" means any molecule which will recognize and bind CD86.

As used herein a "non-CTLA4 molecule" means any molecule which can be attached or joined to the extracellular domain of CTLA4 and does not interfere with CTLA4 binding to its target. These molecules include a polypeptide tag, an immunoglobulin (Ig) tail, a biologically or chemically active protein such as the papillomavirus E7 gene product, melanoma-associated antigen p97, and HIV env protein or a sequence of amino acids which renders soluble and active the extracellular portion of CTLA4 or mutagenized forms thereof.

In order that the invention herein described may be more fully understood, the following description is set forth.

Compositions of the Invention

The invention provides CTLA4 mutant molecules reactive with the CD80 antigen, wherein in the extracellular domain of CTLA4 the first tyrosine in the amino acid motif MYPPPY (SEQ ID NO 11) is replaced by an amino acid other than tyrosine. CTLA4 mutant molecules may be embodied in many forms. The only limitation being that it retain its ability to bind CD80.

In one embodiment of the invention, the CTLA4 mutant molecule is a functional, soluble CTLA4 mutant molecule. The extracellular domain of CTLA4 is an example of a soluble CTLA4 mutant molecule. In one example, the soluble CTLA4 mutant molecule binds the CD80 antigen but does not bind the CD86 antigen.

In a further embodiment of the invention, the soluble CTLA4 mutant molecule has the extracellular domain of mutagenized CTLA4 joined to a non-CTLA4 molecule (also referred to as CTLA4 mutant fusion proteins) such as a polypeptide tag. Other embodiments of soluble CTLA4 molecules include those having the extracellular domain of mutagenized CTLA4 fused or joined with a portion of a biologically or chemically active protein such as the papillomavirus E7 gene product, melanoma-associated antigen p97, and HIV env protein.

In accordance with the practice of this invention, CTLA4 mutant and homolog molecules of the invention may have other amino acid substitutions and still retain the functional property of CTLA4 mutant molecules, namely, the molecule having such substitutions will still bind the CD80 antigen. These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Methods for Making the Compositions of the Invention

The techniques for cloning and expressing DNA sequences encoding the amino acid sequences corresponding to the CTLA4 mutant molecules, e.g., synthesis of oligonucleotides, PCR, transforming cells, constructing vectors, expression systems, and the like are well-established in the art, and most practitioners are familiar with the standard resource materials for specific conditions and procedures. However, the following paragraphs are provided for convenience and notation of modifications of standard techniques where necessary, and may serve as a guideline.

Cloning and Expression of Coding Sequences for Receptors and Fusion Proteins

Constructs corresponding to CTLA4 mutant molecules of the present invention were prepared as described by Linsley et al., *J. Exp. Med.* 173:721–730 (1991), incorporated by reference herein. Alternatively, cDNA clones may be prepared from RNA obtained from cells expressing B7 antigen and CD28 receptor based on knowledge of the published sequences for these proteins (Aruffo and Seed, *Proc. Natl. Acad. Sci.* 84:8573–8577 (1987), and Freeman et al. "Murine B7-2, an Alternative CTLA4 Counter-Receptor that Co-Stimulates T-cell Proliferation and Interleukin 2 Production" (1993) *Journal of Experimental Medicine* 178(6):2185–92) using standard procedures.

CTLA4 mutant molecules consisting of DNA encoding amino acid sequences corresponding to the extracellular domain of mutagenized CTLA4 and the hinge, CH2 and CH3 regions of human IgCγ1 were constructed by ligation of PCR fragments. The cDNA encoding the amino acid sequences is amplified using the polymerase chain reaction ("PCR") technique (U.S. Pat. Nos. 4,683,195 and 4,683,202 to Mullis et al. and Mullis & Faloona, *Methods Enzymol.* 154:335–350 (1987)). CTLA4Ig mutant fusion polypeptides were obtained having DNA encoding amino acid sequences from about position 1 to about position 125 of the extracellular domain of CTLA4 and corresponding to the hinge, CH2 and CH3 regions of IgCγ1.

PCR cDNA made from the total cellular RNA of several human leukemia cell lines was screened, using as primers, oligonucleotides from the published sequence of the CTLA4 gene (Dariavach et al., supra). Of the cDNA tested, H38 cells (an HTLV II-associated leukemia line) provided the best yield of PCR products having the expected size. Since a signal peptide for CTLA4 was not identified in the CTLA4 gene, the N terminus of the predicted sequence of CTLA4 was fused to the signal peptide of oncostatin M (Malik et al., *Molec. and Cell. Biol.* 9:2847 (1989)) in two steps using oligonucleotides. The product of the PCR reaction was ligated with cDNA encoding the amino acid sequences corresponding to the hinge, CH2 and CH3 regions of IgCγ1 into a expression vector, such as CDM8 or πLN.

To obtain DNA encoding full length human CTLA4, a cDNA encoding the transmembrane and cytoplasmic domains of CTLA4 was obtained by PCR from H38 cells and joined with a fragment from CTLA4Ig, obtained as described above, encoding the oncostatin M signal peptide fused to the N terminus of CTLA4, using oligonucleotide primers as described in the Examples, infra. PCR fragments were ligated into the plasmid CDM8, resulting in an expression plasmid encoding the full length CTLA4 gene, and designated OMCTLA4.

To generate mutations in specific regions of the CTLA4 sequence, site-directed mutagenesis was performed on the πLN vector which contained the soluble chimeric form of CTLA4 (CTLA4Ig) in which the extracellular domain of CTLA4 was genetically fused to the hinge and constant regions of a human IgG heavy chain (Linsley et al, *J. Exp. Med.* 173:721–730 (1991)). The CTLA4Ig site-directed mutants were prepared by encoding the desired mutation in overlapping oligonucleotide primers and generating the mutants by PCR (Ho et al., 1989, supra.) using the πLN CTLA4Ig plasmid construct as a template.

In order to generate a comprehensive series of mutants which were directed at the extracellular domain, the codon of the first tyrosine in the MYPPPY (SEQ ID NO 11) motif was changed in order to generate new codons encoding each of the other nineteen amino acids. As this motif appears to be crucial for the CTLA-B7 ligand interactions, all CTLA4 molecules which contain these mutations will have an altered ability to bind the B7 antigens.

To produce large quantities of cloned DNA, vectors containing mutant CTLA4 DNA of the invention were transformed into suitable host cells, such as the bacterial cell line *E. coli* strain MC1061/p3 (Invitrogen Corp., San Diego, Calif.) using standard procedures, and colonies are screened for the appropriate plasmids.

The clones containing mutant CTLA4 DNA obtained as described above are then transfected into suitable host cells for expression. Depending on the host cell used, transfection is performed using standard techniques appropriate to such cells. For example, transfection into mammalian cells is accomplished using DEAE-dextran mediated transfection, $CaPO_4$ co-precipitation, lipofection, electroporation, or protoplast fusion, and other methods known in the art including: lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Expression in eukaryotic host cell cultures derived from multicellular organisms is preferred (*Tissue Cultures*, Academic Press, Cruz and Patterson, Eds. (1973)). These systems have the additional advantage of the ability to splice out introns and thus can be used directly to express genomic fragments. Useful host cell lines include Chinese hamster ovary (CHO), monkey kidney (COS), VERO and HeLa cells. In the present invention, cell lines stably expressing the fusion constructs are preferred.

Expression vectors for such cells ordinarily include promoters and control sequences compatible with mammalian cells such as, for example, CMV promoter (CDM8 vector) and avian sarcoma virus (ASV) (πLN vector). Other commonly used early and late promoters include those from Simian Virus 40 (SV 40) (Fiers, et al., *Nature* 273:113 (1973)), or other viral promoters such as those derived from polyoma, Adenovirus 2, and bovine papilloma virus. The controllable promoter, hMTII (Karin, et al., *Nature* 299:797–802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eukaryotes.

Although preferred host cells for expression of the fusion constructs include eukaryotic cells such as COS or CHO cells, other eukaryotic microbes may be used as hosts. Laboratory strains of *Saccharomyces cerevisiae*, Baker's yeast, are most used although other strains such as *Schizosaccharomyces pombe* may be used. Vectors employing, for example, the 2$\mu$ origin of replication of Broach, *Meth. Enz.* 101:307 (1983), or other yeast compatible origins of replications (for example, Stinchcomb et al., *Nature* 282:39 (1979)); Tschempe et al., *Gene* 10:157 (1980); and Clarke et al., *Meth. Enz.* 101:300 (1983) ) may be used. Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the CMV promoter provided in the CDM8 vector (Toyama and Okayama, *FEBS* 268:217–221 (1990); the promoter for 3-phosphoglycerate kinase (Hitzeman et al., *J. Biol. Chem.* 255:2073 (1980) ), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* 198: 1056 (1977) ), the tryptophan (trp) promoter system (Goeddel et al., *Nucleic Acids Res.* 8:4057 (1980)) and the lambda derived $P_L$ promoter and N-gene ribosome binding site (Shimatake et al., *Nature* 292:128 (1981)).

The nucleotide sequences encoding CTLA4 mutant molecules may be expressed in a variety of systems as set forth below. The cDNA may be excised by suitable restriction enzymes and ligated into suitable prokaryotic or eukaryotic expression vectors for such expression. The expression of CTLA4 mutant molecules as fusion proteins permits dimer formation of these proteins.

Expression of the mutant CTLA4 receptor of the invention is accomplished transfecting a cell line such as COS cells, and detecting expression by binding of the CTLA4-transfected cells to a ligand for the CTLA4 receptor, for example by testing for binding of the cells to B7Ig fusion protein. Expression of the mutant CTLA4Ig fusion protein of the invention is accomplished by transfecting a cell line such as COS cells, and detecting expression by testing for binding of the mutant CTLA4Ig fusion protein to cells expressing the appropriate ligand.

Sequences of the resulting constructs are confirmed by DNA sequencing using known procedures, for example as described by Sanger et al., *Proc. Natl. Acad. Sci. USA* 74:5463 (1977), as further described by Messing et al., *Nucleic Acids Res.* 9:309 (1981), or by the method of Maxam et al. *Methods Enzymol.* 65:499 (1980)).

Construction and Expression of Soluble CTLA4 Mutant Molecules

The appropriate DNA fragments of CTLA4 mutant molecules and the protein partners or tags (e.g., biologically or chemically active molecules such as ovalbumin, p97, E7, and env pg120) can be isolated from the cDNA by PCR ((U.S. Pat. Nos. 4,683,195 and 4,683,202 to Mullis et al. and Mullis & Faloona, *Methods Enzymol.* 154:335–350 (1987)).

DNA for the fusion proteins of CTLA4 can be prepared by ligating DNA of CTLA4 with that of the various protein tags. In ELISA and FACS assays, the binding and expression of the soluble CTLA4 mutant molecules was detected using antibodies directed against the tag, e.g., ovalbumin, env pg120, HPV E7, and p97.

The DNA sequence of the ovalbumin gene is known (Schweers et al. J. Biol. Chem. (1990) 265(13):7590–5); the DNA sequence of the E7 papillovirus oncogene is known (Tindle et al. J. Gen. Vir. (1990) 71:1347–54; the DNA sequence of the melanoma-asociated antigen p97 is known (Kahn et al. J. Immunol. (1991) 146(9):3235–41); the DNA sequence of env gp120 is known (Wain-Hobson et al. "Nucleotide sequence of AIDS virus LAV" Cell (1985) 40:9–17; Ratner et al. "Complete nucleotide sequence of the AIDS virus HTLV3" Nature 313:277–284 (1985)). The identity of the resulting genes for each of the soluble molecules (i.e., fusion proteins) can be confirmed by DNA sequencing.

The cDNA of the fusion proteins can be expressed either in mammalian (cos, DEAE dextran transfection) or insect (baculovirus transfection) cell lines (Jones et al. Nature (1986) 523:346). The supernatants of the transfected cell lines were harvested, assayed and the fusion proteins then purified by affinity chromatography.

Recovery of Protein Products

DNA encoding the amino acid sequence corresponding to the extracellular domains of CTLA4, including the codons for a signal sequence such as that of oncostatin M in cells capable of appropriate processing is fused with DNA encoding the amino acid sequence corresponding to the Fc domain of a naturally dimeric protein. Purification of these fusion protein products after secretion from the cells is thus facilitated using antibodies reactive with the anti-immunoglobulin portion of the fusion proteins. When secreted into the medium, the fusion protein product is recovered using standard protein purification techniques, for example by application to protein A columns.

Uses of the Compositions of the Invention

CTLA4 proteins which have specific amino acid substitutions at the position of the first tyrosine in the MYPPPY (SEQ ID NO 11) motif have unique binding abilities. Mutants which are generated by replacing this tyrosine with for example either phenylalanine or tryptophan have the capability of discriminating between the B7 antigens. Specifically, these mutant molecules will bind the B7-1 (CD80) antigen but not the B7-2 (CD86) antigen. Therefore these mutant molecules may be used to distinguish between these two antigens. In addition, these mutants may be used to differentially affect the specific biological processes which are mediated by the different B7 antigens.

CTLA4 mutant molecule and/or fragments thereof may be used to react with B7 positive cells, such as B cells, to regulate immune responses mediated by T cell interactions with the B7 antigen positive cells or in vitro for leukocyte typing so as to define B cell maturational stages and/or B cell associated diseases (Yokochi et al. J. Immuno. 128(2):823). Surface immunostaining of leukocytes is accomplished by immunofluorescent technology or immunoenzymatic methods but other means of detection are possible.

Soluble CTLA4 mutant molecules, and/or fragments and derivatives of these proteins, may also be used to react with B7 positive cells, including B cells, to regulate immune responses mediated by T cell dependent B cell responses. The term "fragment" as used herein means a portion of the amino acid sequence encoding the protein referred to as "CTLA4" capable of binding B7. A fragment of the soluble CTLA4 mutant molecule that may be used is a polypeptide having an amino acid sequence corresponding to some portion of the amino acid sequence corresponding to the CTLA4 receptor used to obtain the soluble CTLA4 protein as described herein.

In one embodiment, CTLA4 mutant molecules may be introduced in a suitable pharmaceutical carrier in vivo, i.e. administered into a subject for treatment of pathological conditions such as immune system diseases or cancer (Pearson et al. "Transplantation Tolerance Induced by CTLA4-Ig" *Transplantation,* 1994 Jun. 27, 57(12):1701–6; Bolling et al. "The Effect of Combinations Cyclosporine and CTLA4-Ig Therapy on Cardiac Allograft Survival", *Journal of Surgical Research,* 1994 57(1):60–4).

Introduction of CTLA4 mutant molecules in vivo is expected to result in interference with T cell interactions with other cells, such as B cells, as a result of binding of the ligand to B7 positive cells. The prevention of normal T cell interactions may result in decreased T cell activity, for example, decreased T cell proliferation. In addition, administration of the mutant fusion protein in vivo is expected to result in regulation of in vivo levels of cytokines, including, but not limited to, interleukins, e.g. interleukin ("IL")-2, IL-3, IL-4, IL-6, IL-8, growth factors including tumor growth factor ("TGF"), colony stimulating factor ("CSF"), interferons ("IFNs"), and tumor necrosis factor ("TNF") to promote desired effects in a subject. For example, when the fusion protein is introduced in vivo, it may block production of cytokines, which contribute to malignant growth, for example of tumor cells. The fusion protein may also block proliferation of viruses dependent on T cell activation, such as the virus that causes AIDS, HTLV1.

Under some circumstances, as noted above, the effect of administration of the CTLA4 mutant molecule or its fragments in vivo is inhibitory, resulting from blocking by the fusion protein of the CTLA4 and CD28 triggering resulting from T cell/B cell contact. For example, the CTLA4 mutant molecule may block T cell proliferation. Introduction of the CTLA4 mutant molecule in vivo will thus produce effects on both T and B cell-mediated immune responses. The fusion protein may also be administered to a subject in combination with the introduction of cytokines or other therapeutic reagents.

In an additional embodiment of the invention, other reagents, including derivatives reactive with the CTLA4 mutant molecule are used to regulate T cell interactions. For example, antibodies, and/or antibody fragments reactive with the CTLA4 receptor may be screened to identify those capable of inhibiting the binding of the CTLA4 mutant molecule to the B7-1 antigen. The antibodies or antibody fragments such as Fab or F(ab')$_2$ fragments, may then be used to react with the T cells, for example, to inhibit T cell proliferation.

In another embodiment, the CTLA4 mutant molecule may be used to identify additional compounds capable of regulating the interaction between CTLA4 or CD28 and the B7 antigens. Such compounds may include small naturally occurring molecules that can be used to react with B cells and/or T cells. For example, fermentation broths may be tested for the ability to inhibit CTLA4/B7 interactions. In addition, derivatives of the CTLA4Ig mutant fusion protein as described above may be used to regulate T cell proliferation. For example, the fragments or derivatives may be used to block T cell proliferation in graft versus host (GVH) disease which accompanies allogeneic bone marrow transplantation.

The CD28-mediated T cell proliferation pathway is cyclosporine-resistant, in contrast to proliferation driven by the CD3/Ti cell receptor complex (June et al., *Mol. Cell. Biol.* 7:4472–4481 (1987)). Cyclosporine is relatively ineffective as a treatment for GVH disease (Storb, *Blood* 68:119–125 (1986)). GVH disease is thought to be mediated by T lymphocytes which express CD28 antigen (Storb and Thomas, *Immunol. Rev.* 88:215–238 (1985)). Thus, the CTLA4 mutant molecules may be useful alone, or in combination with immunosuppressants such as cyclosporine, for blocking T cell proliferation in GVH disease, and to treat other pathological conditions such as autoimmunity, transplantation rejection, infectious diseases and neoplasia.

The mutant CTLA4 molecules described herein may be formulated in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. (Quantitative Comparison of Toxicity of Anticancer Agents in Mouse, Rat, Hamster, Dog, Monkey and Man. Cancer Chemother, Rep., 50, No.4, 219–244, May 1966).

Adjustments in the dosage regimen may be made to optimize the growth inhibiting response. Doses may be divided and administered on a daily basis or the dose may be reduced proportionally depending upon the situation. For example, several divided doses may be administered daily or the dose may be proportionally reduced as indicated by the specific therapeutic situation.

In accordance with the practice of the invention an effective amount for treating a subject may be between about 0.1 and about 10 mg/kg body weight of subject. Also, the effective amount may be an amount between about 1 and about 10 mg/kg body weight of subject.

ADVANTAGES OF THE INVENTION: CTLA4 mutant molecules of the invention are expected to be useful in vivo as an inhibitor of T cell activity, over non-specific inhibitors such as cyclosporine and glucosteroids.

The B7-1 (CD80) antigen expressed on activated B cells and cells of other lineages, and the CTLA4 receptor expressed on T cells, can directly bind to each other, and this interaction can mediate cell-cell interaction. The B7-2 (CD86) antigen expressed on activated B cells and cells of other lineages, and the CD28 receptor expressed on T cells, can directly bind to each other, and this interaction can mediate cell-cell interaction. While B7-1 has a greater specificity for CTLA4 and B7-2 has a greater specificity for CD28, these is a certain amount of cross-reactivity between these ligands (Kuchroo et al., Cell, 80:707–718 (1995)).

Interactions between these ligands directly trigger the activation pathways in T cells, leading to cytokine production, T cell proliferation, and B cell differentiation into immunoglobulin producing cells. The activation of B cells that occurs, can cause increased expression of B7 antigen and further CD28 stimulation, leading to a state of chronic inflammation such as in autoimmune diseases, allograft rejection, graft versus host disease or chronic allergic reactions. Blocking or inhibiting this reaction may be effective in preventing T cell cytokine production and thus preventing or reversing inflammatory reactions.

Soluble CTLA4 molecules have been shown previously to be a potent inhibitor of in vitro lymphocyte functions requiring T and B cell interaction (see parent application, U.S. Ser. No. 08/228,208). This indicates the importance of interactions between the B7 antigens and their counter-receptors, CTLA4 and/or CD28.

Recent data suggests that the B7-1 and B7-2 molecules differentially activate distinct T-cell subsets. Specifically, these antigens are linked to the differentiation of the CD4 T-helper cells, which upon stimulation, differentiate into two distinct subpopulations (designated Th1 and Th2), each producing its own set of cytokines and mediating separate effector functions. Significantly, these different subsets appear to play specific roles in a number of clinical pathologies (Cohen, J. Science 262, 175–176 (1993) and Simon et al, P.N.A.S. 91, 8562–8566 (1994)). By influencing the effector functions of these T-cell subsets, CTLA4 mutants molecules may prevent or reverse these types of pathologies.

Under conditions where T cell/B cell interactions are occurring as a result of contact between T cells and B cells, binding of introduced CTLA4 mutant molecules to react with B7 antigen positive cells, for example B cells, may interfere, i.e. inhibit, the T cell/B cell interactions resulting in regulation of immune responses. Because of this exclusively inhibitory effect, CTLA4 mutant molecules are expected to be useful in vivo as an inhibitor of T cell activity, over non-specific inhibitors such as cyclosporine and glucosteroids.

The following examples are presented to illustrate the present invention and to assist one of ordinary skill in making and using the same. The examples are not intended in any way to otherwise limit the scope of the invention.

EXAMPLE 1

By site-specific and homolog mutagenesis, we have identified regions in CTLA4Ig which are required for its high avidity binding to B7-1. The following is a description of how to make soluble CTLA4/CD28 hybrid fusion proteins which bind B7.

Materials and Methods

Monoclonal antibodies (mAbs). Murine Mab's specific for CTLA4 were prepared and characterized as previously described (Linsley et al. J. Ex. Med., (1992) 176:1595–1604). Antibody 9.3 (anti-CD28) has been described previously ((Hansen et al., *Immunogenetics* 10:247–260 (1980)).

Cell Culture. The preparation of stably transfected B7-1 positive CHO cells has been previously described (Linsley et al., in *J. Exp. Med.* 173:721–730 (1991); P. S. Linsley et al., J. Exp. Med. 174:561 (1991)).

Cells were maintained in DMEM supplemented with 10% fetal bovine serum (FBS), 0.2 mM proline, and 1$\mu$M methotrexate. COS cells were grown in DMEM supplemented with 10 FBS. CTLA4Ig was prepared in CHO cells as previously described (Example 2 of U.S. Ser. No. 08/228, 208).

CTLA4Ig and CD28Ig site-directed mutant expression plasmids. Site-directed mutagenesis was performed on a vector encoding soluble chimeric form of CTLA4 (CTLA4Ig) in which the extracellular domain of CTLA4 was genetically fused to the hinge and constant regions of a human IgG heavy chain (Linsley et al, *J. Exp. Med.* 173:721–730 (1991)). CTLA4Ig site-directed mutants were prepared by encoding the desired mutation in overlapping oligonucleotide primers and generating the mutants by PCR (Ho et al., 1989, supra.) using the CTLA4Ig plasmid construct as a template.

Six mutants were prepared which encoded substitutions to alanine in the highly conserved hexapeptide 98MYP-PPY103 (SEQ ID NO 11) forming part of the putative CDR3-like domain (FIG. 1) (Ho et al., 1989, supra.). These mutants are described in Table II. In addition, two mutants encoding the residues P103A and Y104A (MYPPAY (SEQ ID NO:7) and MYPPPA (SEQ ID NO:8), respectively) from the CD28Ig 99MYPPPY104 (SEQ ID NO 11) hexapeptide using CD28Ig as a template were also prepared by the same method. These mutants are also described in Table II.

Primers required for PCR reactions but not for introducing mutations included (1) a CDM8 forward (CDM8FP) primer encoding a complementary sequence upstream of the HindIII restriction site at the 5' end of the CDM8 stuffer region, and (2) a reverse primer (CDM8RP) encoding a complementary sequence downstream of the XbaI site at the 3' end of the CDM8 stuffer region.

These primers encoded the following sequences:

CDM8FP:5'-AATACGACTCACTATAGG (SEQ ID NO:9)

CDM8RP:5'-CACCACACTGTATTAACC (SEQ ID NO:10)

PCR conditions consisted of 6 min at 94° C. followed by 25 cycles of 1 min at 94° C., 2 min at 55° C. and 3 min at 72° C. Taq polymerase and reaction conditions were used as suggested by the vendor (Perkin Elmer Cetus, Emeryville, Calif.). PCR products were digested with HindIII and XbaI and ligated to HindIII/XbaI-cut CDM8 expression vector.

To confirm that the desired mutations had been inserted and to verify the absence of secondary mutations, each CTLA4Ig mutant fusion protein (an example of a soluble CTLA4 mutant fusion protein) was sequenced by the dideoxy chain termination/extension reaction with Sequenase reagents used according to the manufacturer's recommendations (United States Biochemical Corp., Cleveland, Ohio).

Plasmids were transfected into COS cells (Aruffo et al., *Cell* 61:1303 (1990)) and the conditioned media was used as a source for the resulting Ig mutant fusion proteins.

CTLA4/CD28Ig hybrid expression plasmids. CTLA4/CD28Ig hybrid scan plasmids encoding the constructs HS2, HS4, HS4-A, HS4-B, and HS5 (FIG. 3 and Table I) were prepared by PCR using overlapping oligonucleotide primers designed to introduce CTLA4 sequences into CD28Ig while, at the same time, deleting the equivalent region from CD28. The same CDM8 forward and reverse PCR primers described above were also used.

The following is a list of the CTLA4/CD28 hybrid fusion proteins which were made.

| DESIGNATION | FRAMEWORK | MODIFICATIONS |
|---|---|---|
| HS1 | CTLA4 | 1–24 OF CD28 |
|  |  | 97–125 OF CD28 |
| HS2 | CD28 | 1–22 OF CTLA4 |
|  |  | 96–125 OF CTLA4 |
| HS3 | CTLA4 | 96–125 OF CD28 |
| HS4 | CD28 | 96–123 OF CTLA4 |
| HS4A | CD28 | 96–113 OF CTLA4 |
| HS4B | CD28 | 114–123 OF CTLA4 |
| HS5 | CD28 | 25–32 OF CTLA4 |
| HS6 | CTLA4 | 25–32 OF CD28 |
| HS7 | CD28 | 96–123 OF CTLA4 |
|  |  | 25–32 OF CTLA4 |
| HS8 | CD28 | 25–32 OF CTLA4 |
|  |  | 96–113 OF CTLA4 |
| HS9 | CD28 | 25–32 OF CTLA4 |
|  |  | 114–123 OF CTLA4 |
| HS10 | CD28 | 96–123 OF CTLA4 |
|  |  | 51–58 OF CTLA4 |
| HS11 | CD28 | 25–32 OF CTLA4 |
|  |  | 51–58 OF CTLA4 |
|  |  | 96–123 OF CTLA4 |
| HS12 | CD28 | 51–58 OF CTLA4 |
|  |  | 96–113 OF CTLA4 |
| HS13 | CD28 | 25–32 OF CTLA4 |
|  |  | 51–58 OF CTLA4 |
|  |  | 96–113 OF CTLA4 |
| HS14 | CD28 | 51–58 OF CTLA4 |

Each cDNA construct was genetically linked to cDNA encoding the hinge and constant regions of a human IgG1 in order to make soluble chimeras.

A HS6 hybrid was prepared in a similar manner to that described above except that the CDR1-like region in CTLA4Ig was replaced with the equivalent region from CD28Ig.

HS7, HS8, and HS9 constructs were prepared by replacing a ≈350 base-pair HindIII/HpaI 5' fragment of HS4, HS4-A, and HS4-B, respectively, with the equivalent cDNA fragment similarly digested from HS5 thus introducing the CDR1-like loop of CTLA4 into those hybrids already containing the CTLA4 CDR3-like region.

HS10-HS13 constructs are domain homolog mutants which were prepared by introducing the CDR2-like loop of CTLA4Ig into previously constructed homolog mutants. This was done by overlapping PCR mutagenesis whereby primers were designed to introduce CTLA4 CDR2-like sequences into homolog templates while at the same time deleting the equivalent CD28 CDR2-like region from the molecule.

Figure 3:

Accordingly, HS4 served as a template to make HS10; HS7 served as a template to make HS11; HS4-A served as a template to make HS12; and HS8 served as a template to make HS13 (FIG. 3 and Table I). The CDM8 primers described above were also used in these constructions.

The HS14 hybrid construct was prepared by replacing the CDR2-like loop of CD28 with the equivalent loop from CTLA4Ig (FIG. 3 and Table I).

Oligonucleotide primers designed to introduce these changes were used in overlapping PCR mutagenesis identical to that described for other mutants.

PCR reactions and subcloning into CDM8 were performed as described above. Again all mutants were sequenced by the dideoxy chain termination/extension reaction.

Plasmids encoding each of the mutants were transfected into COS cells and the resulting soluble Ig fusion proteins were quantitated in culture media and visualized by Western blot as described in following sections.

Quantitation of the resulting Ig fusion proteins in culture media. Soluble mutant fusion proteins were quantitated in an enzyme immunoassay by determining the amount of Ig present in serum-free COS cell culture media.

Microtiter plates (Immulon2; Dynatech Labs., Chantilly, Va.) were coated with 0.5 µg/ml goat anti-human IgG (Jackson Immunoresearch Labs., West Chester, Pa.) for 16–24 h at 4° C. Wells were blocked for 1 h with specimen diluent (Genetic Systems, Seattle, Wash.), then washed with PBS containing 0.05% Tween 20 (PBS-Tw).

COS cell culture media containing fusion proteins was added at various dilutions and incubated for 1 h at 22° C. Known concentrations of CTLA4Ig were also added to separate wells on each plate for a standard curve.

After washing, horseradish peroxidase (HRP)-conjugated goat anti-human IgG (Tago, Burlingame, Calif.) diluted 1:12,000 was added and incubated for 1 h at 22° C. Wells were then washed and incubated with 3,3',5,5' tetramethylbenzidine (TMB) substrate (Genetic Systems) for 15 min before stopping the reaction by the addition of 1N $H_2SO_4$. Optical density was measured at dual wavelengths of 450 and 630 nm on a microtiter plate reader (Genetic Systems).

Concentration of mutant Ig fusion protein was determined by comparison with a standard curve of known concentrations of CTLA4Ig.

Immunoprecipitation and Western blot analysis. CTLA4/CD28Ig hybrid fusion proteins present in culture media were adsorbed to protein A-Sepharose by overnight incubation at 4° C. The beads were washed with PBS containing 0.1 Nonidet-P40 (NP40) then SDS PAGE sample buffer was added and the eluted protein was loaded onto an SDS polyacrylamide gel.

Western blot transfer of protein onto nitrocellulose was done by standard procedures. Nitrocellulose membranes were then blocked with PBS containing 0.1% NP40 and 1% non-fat dry milk powder.

After washing in PBS-Tw membranes were incubated with alkaline phosphatase-conjugated goat anti-human IgG (Boehringer Mannheim, Indianapolis, Ind.) diluted 1:1,000 and incubated for 1 h at 22° C. Blots were then washed and developed using standard procedures.

B7 positive CHO cell enzyme immunoassay. The ability of CTLA4Ig mutant fusion proteins, and CTLA4/CD28Ig hybrid fusion proteins to bind B7-1 stably expressed on CHO cells was determined by an enzyme immunoassay.

Round bottom tissue culture treated 96 well microtiter plates (Corning, Corning, N.Y.) were seeded with B7-1 positive CHO cells at $10^3$ cells/well. Two days later the confluent cells were fixed in 95% ethanol for 15 min.

After washing with PBS-Tw, mutant Ig fusion proteins were added at various concentrations and incubated for 1 h at 4° C. After washing, HRP-conjugated goat anti-human IgG (Tago) diluted 1:10,000 was added and incubated for 1 h at 22° C.

Wells were then washed and TMB substrate added as above and allowed to react for 30 min before stopping the reaction with 1N $H_2SO_4$.

Absorbance of the wells was measured at 450 nm.

CD28Ig site-directed mutant fusion protein binding assay. Site-directed mutant fusion proteins of CD28Ig were assayed for their ability to bind to B7-1 by an indirect enzyme immunoassay.

Wells of ELISA plates were coated with a chimeric fusion protein containing the extracellular domain of human B7-1 fused to a mouse IgG1 Fc region, at 5 µg/ml for 16 h at 4° C. Wells were blocked for 1 h with specimen diluent (Genetic Systems) then washed with PBS-Tw. COS cell culture media containing known concentrations of mutant fusion protein was added at various concentrations and incubated for 1 h at 22° C.

Known concentrations of CD28Ig were also added to separate wells on each plate. After washing, HRP-conjugated goat anti-human IgG (Tago) diluted 1:10,000 was added and incubated for 1 h at 22° C. TMB substrate was added and optical densities read as described for quantitation of Ig fusion proteins in culture media.

mAb binding to Ig fusion proteins. The ability of anti-CTLA4 mAb's and the anti-CD28 mAb 9.3 to bind CTLA4/CD28Ig hybrid fusion proteins and CTLA4Ig mutant fusion proteins was assessed by an enzyme immunoassay.

Wells of microtiter plates (Immulon 2) were coated with 0.5 µg/ml of goat anti-human IgG (Jackson) for 16–24 h at 4° C. Plates were blocked for 1 h with specimen diluent (Genetic Systems), washed with PBS-Tw, then incubated with the Ig fusion proteins for 1 h at 22° C. After washing, wells were incubated with mAb at 1 µg/ml for 1 h at 22° C.

After further washing, HRP-conjugated goat anti-mouse Ig (Tago) diluted 1:10,000 was added and incubated for 1 h at 22° C. TMB substrate was added and optical density measured as described above.

CTLA4 molecular model. An approximate three-dimensional model of the CTLA4 extracellular domain was generated based on the conservation of consensus residues of IGSF variable-like domains.

Figure 6:
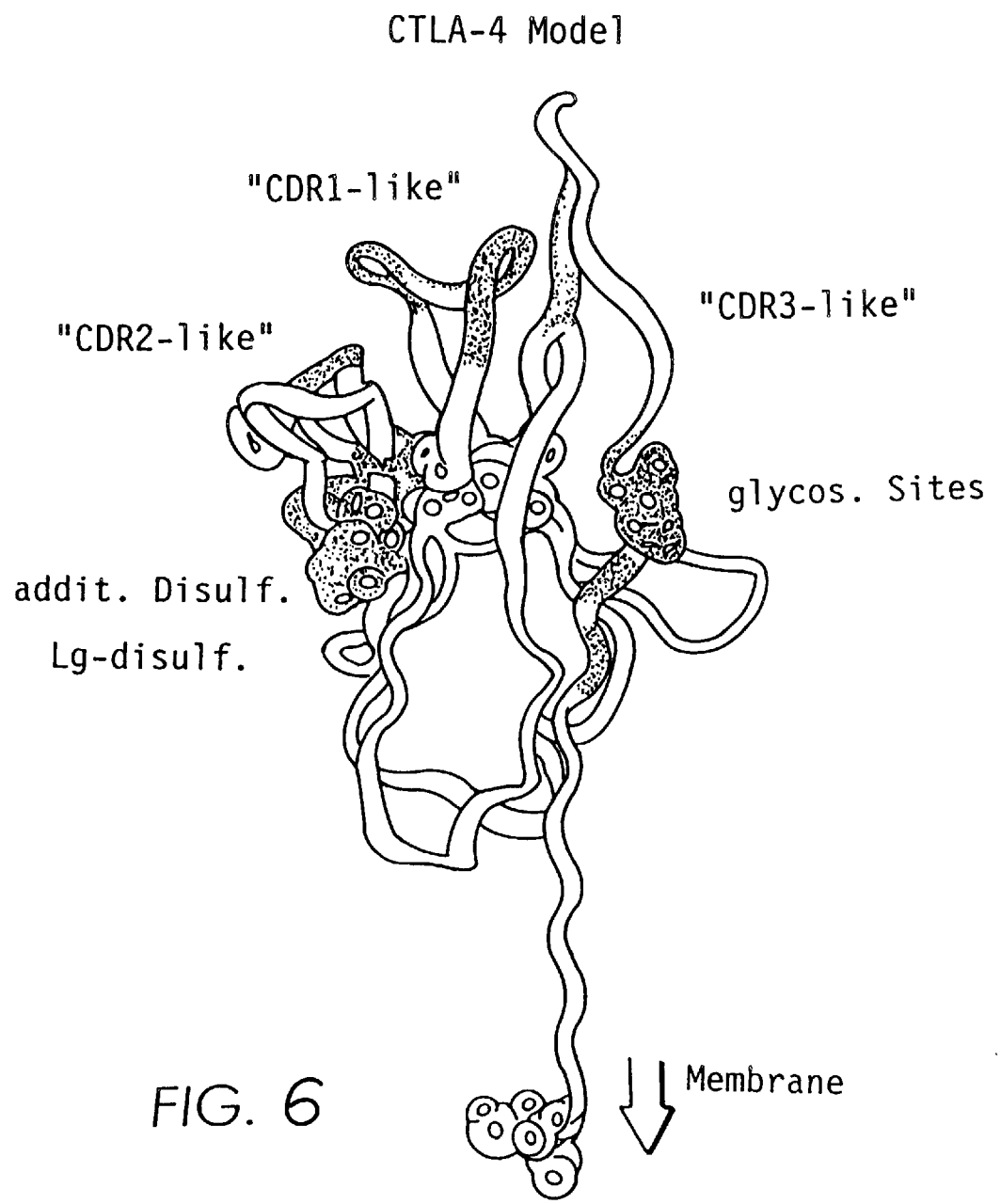

Using such IGSF consensus residues as "anchor points" for sequence alignments, CTLA4 residues were assigned to the A, B, C, C', C", D, E, F, G strands of an Ig variable fold (Williams/Barclay, 1988, supra.) and the connecting loop regions (FIG. 6).

The CTLA4 model was built (InsightII, Discover, Molecular Modeling and Mechanics Programs, respectively, Biosym Technologies, Inc., San Diego) using the variable heavy chain of HyHEL-5 (Sheriff et al., 1987 PNAS 84:8075–8079) as template structure. Side-chain replacements and loop conformations were approximated using conformational searching (Bruccoleri et al., 1988 335:564–568).

Several versions of the model with modified assignments of some residues to β-strands or loops were tested using 3D-profile analysis (Lüthy et al., 1992, Nature 336:83–85) in order to improve the initial alignment of the CTLA4 extracellular region sequence with an IGSF variable fold.

Results

Construction and binding activity of CTLA4Ig and CD28Ig mutant fusion proteins. A sequence alignment of various homologues of CD28 and CTLA4 is demonstrated in FIG. 1. In FIG. 1, sequences of human (H), mouse (M), rat (R), and chicken (Ch) CD28 are aligned with human and mouse CTLA4. Residues are numbered from the mature protein N-terminus with the signal peptides and transmembrane domains underlined and the CDR-analogous regions noted. Dark shaded areas highlight complete conservation of residues while light shaded areas highlight conservative amino acid substitutions in all family members.

Regions of sequence conservation are scattered throughout the extracellular domains of these proteins with the most rigorous conservation seen in the hexapeptide MYPPPY (SEQ ID NO:11) motif located in the CDR3-like loop of both CTLA4 and CD28 (FIG. 1). This suggests a probable role for this region in the interaction with a B7 antigen, e.g., B7-1 and B7-2.

To test this possibility, site-directed alanine scanning mutations were introduced into this region of CTLA4Ig using PCR oligonucleotide primer-directed mutagenesis thereby resulting in CTLA4Ig mutant fusion proteins. Similarly two alanine mutations were introduced into the CD28Ig MYPPPY (SEQ ID NO 11) motif thereby resulting in CD28Ig mutant fusion proteins.

All cDNA constructs were sequenced to confirm the desired mutations before transfection into COS cells. The concentrations of mutant Ig fusion proteins in serum-free COS cell culture media were determined by an Ig quantitation assay.

The ability of each CTLA4Ig mutant fusion protein to bind to B7-1 expressed on stably transfected CHO cells was then determined by an indirect cell binding immunoassay. Binding of CD28Ig mutant fusion proteins to B7-1 was assessed by an indirect enzyme immunoassay. Each of these assays are described in Materials and Methods.

Mutagenesis of each residue of the CTLA4Ig MYPPPY (SEQ ID NO 11) motif to Ala had a profound effect on binding to B7-1 as shown in FIG. 2. FIG. 2 shows that mutations in the MYPPPY (SEQ ID NO 11) motif of CTLA4Ig and CD28Ig disrupt binding to B7-1. Site-directed mutant Ig fusion proteins were produced in transiently transfected COS cells, quantitated and tested for their ability to bind to B7-1.

In FIG. 2 fusion protein quantitations were repeated at least twice with replicate determinations. Specifically, FIG. 2 shows that CTLA4Ig mutants bind to stably transfected, ethanol-fixed B7-1+ CHO cells grown to confluency in ELISA tissue culture plates. Binding data is expressed as the average of duplicate wells and is representative of at least two experiments.

Y99A and P101A mutants bound to B7-1 but with considerably reduced ability relative to wild-type CTLA4Ig. In contrast, the mutants M98A, P100A, P102A and Y103A showed an almost complete loss of binding. Furthermore, the CD28Ig MYPPPY (SEQ ID NO 11) mutants P103A and Y104A did not display detectable binding to B7-1 immobilized on wells of ELISA plates (FIG. 2).

B7-1 transfected CHO cells which were incubated with CTLA4Ig mutant fusion protein, labeled with anti-human FITC, and assayed using a FACSCAN showed equivalent results. These results clearly demonstrate a critical role for the MYPPPY (SEQ ID NO 11) motif in both CTLA4Ig and CD28Ig binding to B7-1.

Characterization of CTLA4/CD28Ig hybrid fusion proteins. Since the MYPPPY (SEQ ID NO 11) motif is common to both CTLA4Ig and CD28Ig, it alone cannot account for the observed differences in binding to B7-1 seen with CTLA4Ig and CD28Ig. The contribution of less well conserved residues to high avidity binding B7-1 was assessed using a series of homolog mutants.

The three CDR-like regions of CD28 were replaced in various combinations with the equivalent regions from the CTLA4 extracellular domain (FIG. 3 and Table I). FIG. 3 is a map of CTLA4/CD28Ig mutant fusion proteins showing % binding activity to B7-1+ CHO cells relative to CTLA4Ig. Conserved cysteine residues (C) are shown at positions 22, 93 and 121 respectively (CTLA4 numbering). Also shown is the position of the MYPPPY (SEQ ID NO 11) motif. Open areas represent CD28 sequence; filled areas represent CTLA4 sequence; cross-hatched areas represent beginning of IgG Fc (also refer to Table I). Percent binding activities were determined by comparing binding curves (FIGS. 4/5) relative to CTLA4Ig and finding the concentration of a mutant required to give the same O.D. as that found for CTLA4Ig. The ratio of mutant protein to CTLA4Ig concentration at a particular O.D. was then expressed as % binding activity. At least two A450 readings were taken from the linear part of the CTLA4Ig binding curve and the average % binding activity determined.

A total of 14 hybrid cDNA constructs were prepared, sequenced, and transfected into COS cells. Concentrations of Ig fusion proteins in serum-free culture media were determined and their electrophoretic mobility compared by SDS-PAGE including Western blotting analysis.

Under reducing conditions each chimeric protein migrated with a relative molecular mass ranging between that of CTLA4Ig (Mr-50 kDa) and CD28Ig (Mr-70 kDa) depending on the size of the exchanged region.

Under non-reducing conditions the proteins migrated primarily between 100–140 kDa indicating that these fusion proteins existed as disulfide-linked dimers despite mutagenesis of the cysteine residues in the hinge region of the Fc.

Since four of the five conserved cysteine residues in CTLA4 and CD28 are thought to be involved in intrachain disulfide bonds, dimerization of the fusion proteins was therefore most likely attributable to the fifth conserved cysteine residue at position 121 in CTLA4 (position 123 in CD28).

Binding of CTLA4/CD28Ig hybrid fusion proteins to B7-1. The hybrid fusion proteins were tested for their ability to bind to B7-1 by the same indirect cell binding immunoassay used to assay the site-specific CTLA4Ig and CD28Ig mutant fusion proteins.

Figure 4:
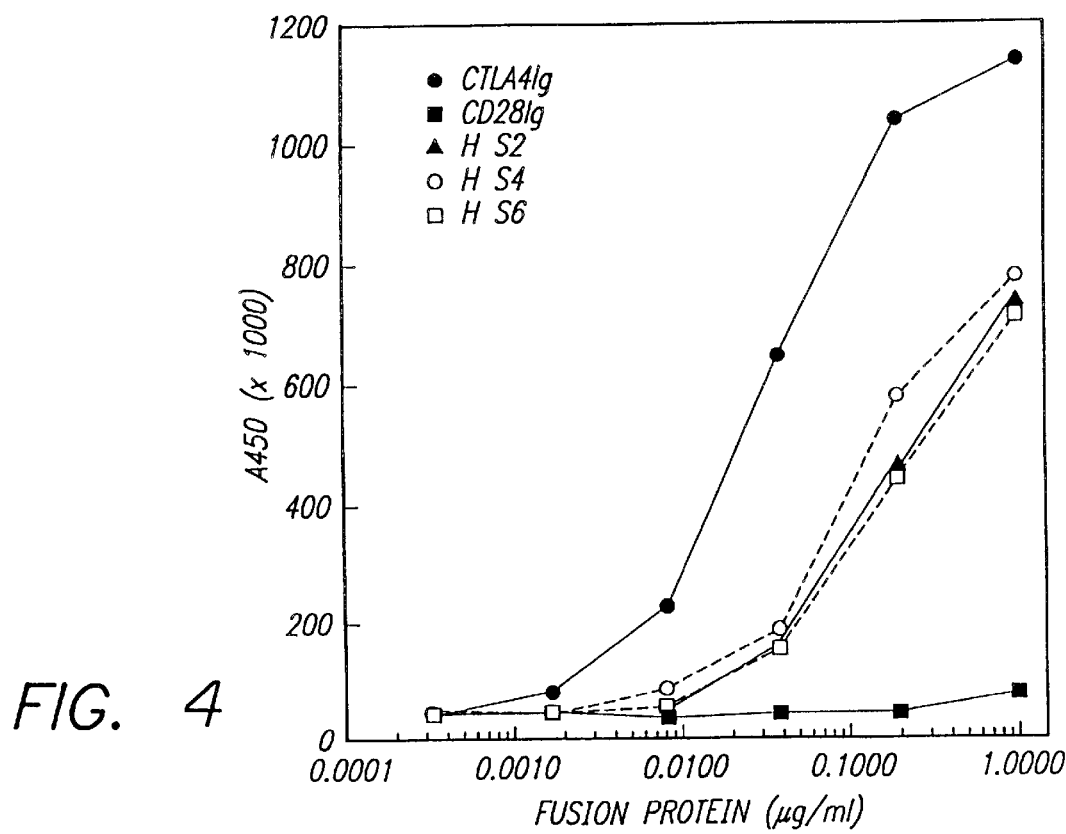

Under these conditions the binding between CD28Ig and B7-1 is barely detectable (FIGS. 4/5). However, replacing residues 97 to 125 (the CDR3-like extended region) of CD28 with the corresponding residues of CTLA4 resulted in an approximately two and a half orders of magnitude increase in binding of the CD28Ig analog to B7-1 (FIGS. 4/5). FIGS. 4/5 shows that CTLA4/CD28Ig mutant fusion proteins demonstrate involvement of CDR-analogous regions in high avidity binding to B7-1 CHO cells. Mutants were assayed as described in FIG. 2. Data is expressed as the average of duplicate wells and is representative of at least three experiments. From these curves % binding activity relative to CTLA4Ig was determined as explained and shown in FIG. 3.

Binding to B7-1 by this construct, termed HS4 (FIG. 3), is approximately five fold less than wild type CTLA4Ig. The HS2 hybrid which includes additional N-terminal residues of CTLA4 (amino acids 1–22), did not improve the ability of the hybrid molecule to bind to B7-1 relative to HS4.

The HS6 construct which represents the CTLA4Ig sequence except that it contains the CDR1-like region of CD28 (residues 25-32), bound similarly. However, the additional inclusion of the CTLA4 CDR1-like region (residues 25–32) into the HS4 construct (termed HS7), showed further improved binding so that the binding affinity is approximately 44% of CTLA4Ig (FIG. 3).

In contrast, inclusion of the CDR2-like region of CTLA4 (residues 51–58) into HS4 (construct HS10), did not further increase binding (FIG. 3). A similar result was found for construct HS11 which had all three CDR-like region sequences of CTLA4 included into CD28Ig. The HS5 hybrid which contained only the CDR1-like domain of CTLA4 bound at very low levels.

Figure 5:
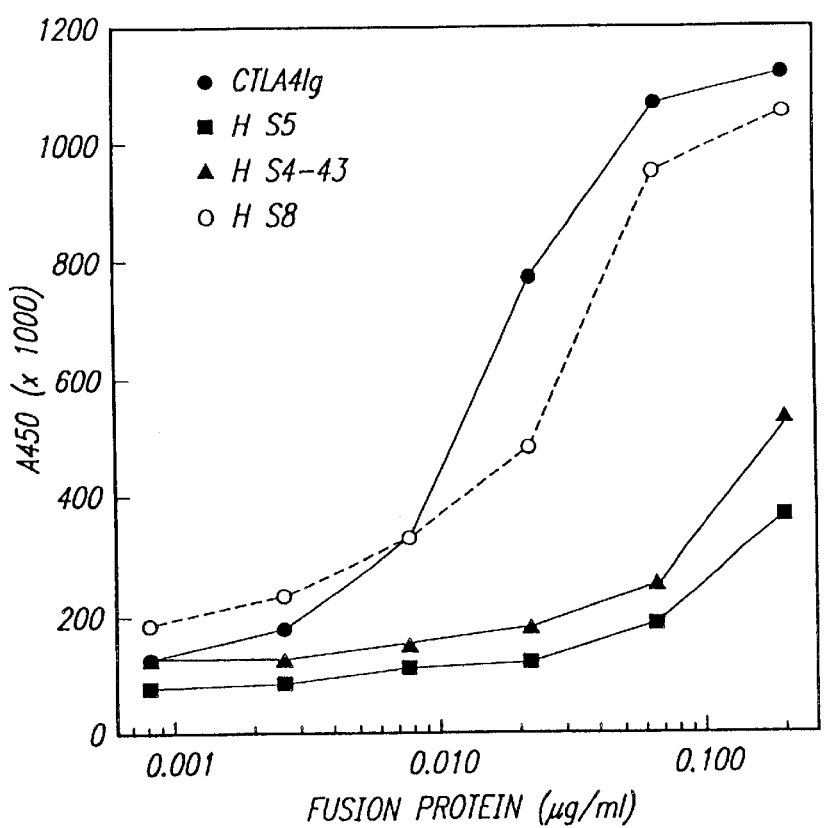

The CTLA4/CD28Ig hybrid HS4-A encoded CTLA4Ig residues 96–113 in the C-terminally extended CDR3-like region; nine CTLA4 derived residues fewer than HS4 (FIG. 3 and Table I). HS4-A bound B7-1 CHO cells less well than HS4 (FIGS. 3 and 5). However, addition of the CTLA4 CDR1-like loop (HS8 hybrid), increased B7-1 binding from about 2% to nearly 60% of wild type binding.

On the other hand, addition of the CTLA4 CDR2-like loop into HS4-A (HS12) did not increase binding relative to HS4-A; neither did addition of all three CTLA4 CDR-like regions (HS13, FIG. 3).

Another hybrid called HS4-B, encoded the CD28 CDR3-like region including the MYPPPY (SEQ ID NO 11) motif followed by CTLA4 residues 114–122 (Table I and FIG. 3).

HS4-B and HS4-A displayed similar binding to B7-1. Unlike HS4-A, however, the inclusion of the CTLA4 CDR1-like loop into HS4-9 (HS9) did not improve binding (FIG. 3), suggesting that residues immediately adjacent to the CTLA4Ig MYPPPY (SEQ ID NO 11) motif were important determinants in high avidity binding.

Monoclonal antibody binding to CTLA4/CD28Ig hybrid fusion proteins. The structural integrity of each hybrid fusion protein was examined by assessing their ability to bind mAb's specific for CTLA4 or CD28 in an enzyme immunoassay. The CTLA4 specific mAb's 7F8, 11D4 and 10A8 block ligand binding (Linsley et al. (1992) supra.).

These antibodies bound to each of the CTLA4Ig mutant fusion proteins except 11D4 which failed to bind to P100A and P102A (Table II). Since 7F8 and 10A8 bound to these mutants, the lack of binding by 11D4 can probably be attributed to mutagenesis perturbing the epitope recognized by 11D4.

Conversely, each antibody failed to bind to any of the homolog scan hybrid fusion proteins except 7F8 which bound to HS6, and 11D4 which bound weakly to HS8. As many of these homolog hybrid fusion proteins were, to some extent, able to bind to B7-1, it is likely that lack of binding by the antibodies was due to disruption of conformational epitopes formed by spatially adjacent but non-linear sequences.

The CD28 specific mAb 9.3 (Linsley et al. (1992) supra.) failed to bind to either of the CD28 site-directed mutant fusion proteins but bound to the hybrid fusion proteins HS4, HS4-A, HS7 and HS8. With HS2, weaker binding was observed. No binding was seen with the HS5 and HS6 constructs.

CTLA4 model. FIG. 6 shows a schematic representation of the CTLA4 model. The assignment of CTLA4 residues to CDR-like regions is shown in FIG. 1. The CTLA4 model suggests the presence of an additional (non-Ig) disulfide bond between residues Cys49 and Cys67 which supports the similarity of CTLA4 and the Ig variable fold.

The two possible N-linked glycosylation sites in CTLA4 map to solvent exposed positions of the Ig β-strand framework regions. 3D-profile analysis indicated that the CTLA4 sequence is overall compatible with an Ig V-fold, albeit more distantly related.

Residue Val115 represents the last residue of the CTLA4Ig-like domain. The conformation of the region between Val115 and the membrane-proximal Cys121 which is thought to form the CTLA4 homodimer is highly variable in the CD28 family. The picture that emerges is that CD28 family members mainly utilize residues in two of three CDR-like regions for binding to B7-1.

The MYPPPY (SEQ ID NO 11) motif represents a conserved scaffold for binding which appears to be augmented by its C-terminal extension and which is specifically modulated by the highly variable CDR1-like region. CDR3 and CDR1-like regions are spatially contiguous in Ig-variable folds. The CDR2 like region is spatially distant and does not, in the case of the CD28 family, significantly contribute to the binding to B7-1.

EXAMPLE 2

By site-specific mutagenesis, we have identified an amino acid position in CTLA4 which plays a crucial role in this molecule's ability to bind both CD80 and CD86. In addition we identify 2 amino acid substitutions at this position which generate mutant CTLA4Ig molecules that have the ability to bind CD80 in a manner similar to the wild type molecule, but have lost the ability to bind CD86. The following is a description of how to make soluble CTLA4 fusion proteins which bind CD80 but not CD86.

Materials and Methods

Monoclonal antibodies (mAbs). Murine monoclonal antibodies specific for CD80 and CD86 have been described previously (Kuchroo et al., *Cell*, Vol. 80, 707–718, (1995)).

Cell Culture. The preparation of stably transfected B7-1 (CD80) positive CHO cells has been previously described (Linsley et al., in *J. Exp. Med.* 173:721–730 (1991); P. S. Linsley et al., J. Exp. Med. 174:561 (1991)). The preparation of stably transfected B7-2 (CD86) cells has been previously described (Freeman et al., *J. Exp. Med.* 178: 2185 (1993); PCT WO95/06738). The preparation of LCL cells has been previously described (Wyss-Coray et al., *European Journal of Immunology,* 23(12), 3350–3357 (1993)).

Cells were maintained in DMEM supplemented with 10% fetal bovine serum (FBS), 0.2 mM proline, and 1 μM methotrexate. COS cells were grown in DMEM supplemented with 10% FBS. CTLA4Ig was prepared in CHO cells as previously described (see parent application, U.S. Ser. No. 08/228,208, Example 2).

CTLA4Ig site-directed mutant expression plasmids. Site-directed mutagenesis was performed on a vector encoding soluble chimeric form of CTLA4 (CTLA4Ig) in which the extracellular domain of CTLA4 was genetically fused to the hinge and constant regions of a human IgG heavy chain (Linsley et al, *J. Exp. Med.* 173:721–730 (1991)). CTLA4Ig site-directed mutants were prepared by encoding the desired mutation in overlapping oligonucleotide primers and generating the mutants by PCR (Ho et al., 1989, supra.) using the πLN CTLA4Ig plasmid construct as a template (see parent application, U.S. Ser. No. 08/228,208, Example 1).

Eighteen mutants were prepared which encode amino acid substitutions at the first tyrosine position in the highly conserved MYPPPY (SEQ ID NO 11) motif of CTLA4 (FIG. 1) (Ho et al., 1989, supra). This series of mutants was generated by manipulating the codon at this position in order to generate new codons encoding each of the twenty amino acids except cysteine.

Primers required for PCR reactions but not for introducing mutations included (1) a πLN forward primer (πLNIgFP) encoding a complementary sequence upstream of the SacI restriction site at the 5' end of the CTLA4Ig πLN sequence, and (2) a reverse primer (πLNIgRP) encoding a complementary sequence downstream of the XbaI site at the 3' end of the immunoglobulin encoding region.

These primers encoded the following sequences:

πLNIgFP:5'-TGCAAGGTGGAGCTCATGTTCCCACCGCCATAC (SEQ ID NO:12)

πLNIgRP:5'-GCGCTCGACTCTAGAAGCATCCTCGTG (SEQ ID NO:13)

PCR conditions consisted of 6 min at 94° C. followed by 30 cycles of 1 min at 94° C., 2 min at 55° C. and 3 min at 72° C. Taq polymerase and reaction conditions were used as suggested by the vendor (Perkin Elmer Cetus, Emeryville, Calif.). PCR products were digested with SacI and XbaI and ligated to SacI/XbaI-cut πLN CTLA4Ig expression vector.

To confirm that the desired mutations had been inserted and to verify the absence of secondary mutations, each CTLA4Ig mutant fusion protein (an example of a soluble CTLA4 mutant fusion protein) was sequenced by the dideoxy chain termination/extension reaction with Sequenase reagents used according to the manufacturers recommendations (United States Biochemical Corp., Cleveland, Ohio).

Plasmids encoding each of the mutants were transfected into COS cells (Aruffo et al., Cell 61:1303 (1990)) and the conditioned media was used as a source for the resulting Ig mutant fusion proteins.

Quantitation of the resulting Ig fusion proteins in culture media. Soluble mutant fusion proteins were quantitated by FACS analysis as previously described (see parent application, U.S. Ser. No. 08/228,208, Example 1).

Binding CTLA4Ig fusion proteins in the presence of anti-CD80 or anti-CD86 mAbs. Binding studies involving CTLA4Ig proteins and competitor molecules utilized previously described procedures (see parent application, U.S. Ser. No. 08/228,208, Example 4).

Purification of Ig fusion proteins. Ig fusion proteins were purified as previously described (See parent application, U.S. Ser. No. 08/228,208, Example 1).

Results

Binding activity of CTLA4Ig mutant fusion proteins. Site-directed mutant Ig fusion proteins were produced in transiently transfected COS cells, quantitated and tested for their ability to bind to CD80 or CD86.

The ability of each CTLA4Ig mutant fusion protein to bind CD80 or CD86 expressed on stably transfected CHO cells was determined by incubating these cells with the different CTLA4Ig mutant fusion proteins, labelling the mutant proteins with anti-human FITC, and assaying them via FACSCAN as described above.

Figure 7:
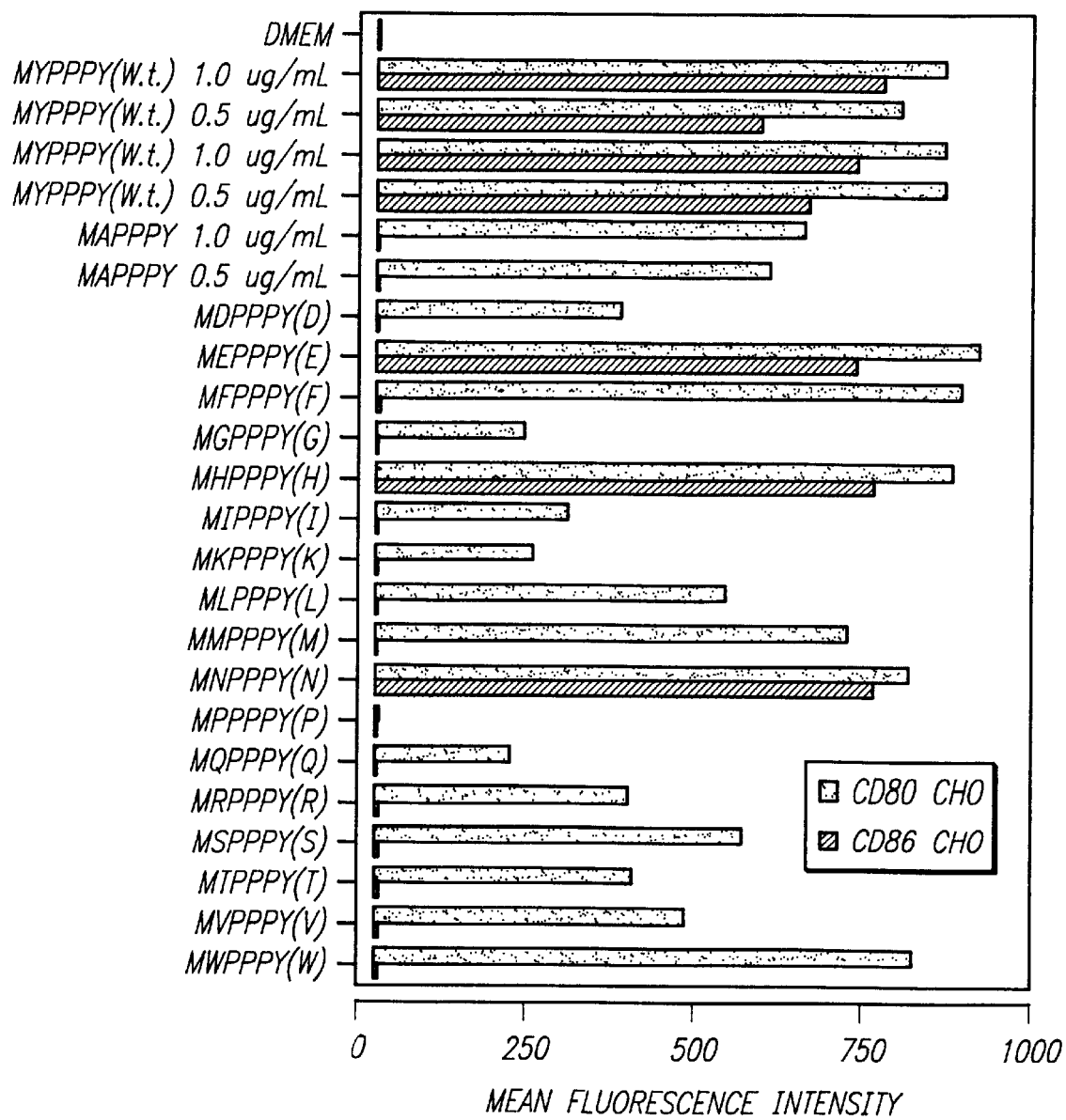

Titration staining of CHO cells which express either CD80 or CD86 shows that mutagenesis of the first tyrosine residue in the CTLA4Ig MYPPPY (SEQ ID NO 11) motif has a profound effect on binding to both CD80 and CD86. FIG. 7 shows that each amino acid substitution at this position produces a unique binding profile. In addition, this figure shows that substitutions with phenylalanine and tryptophan at this position generate mutants that are able to bind CD80 in a manner analogous to the wild type molecule, but are unable to bind CD86.

Figure 8:
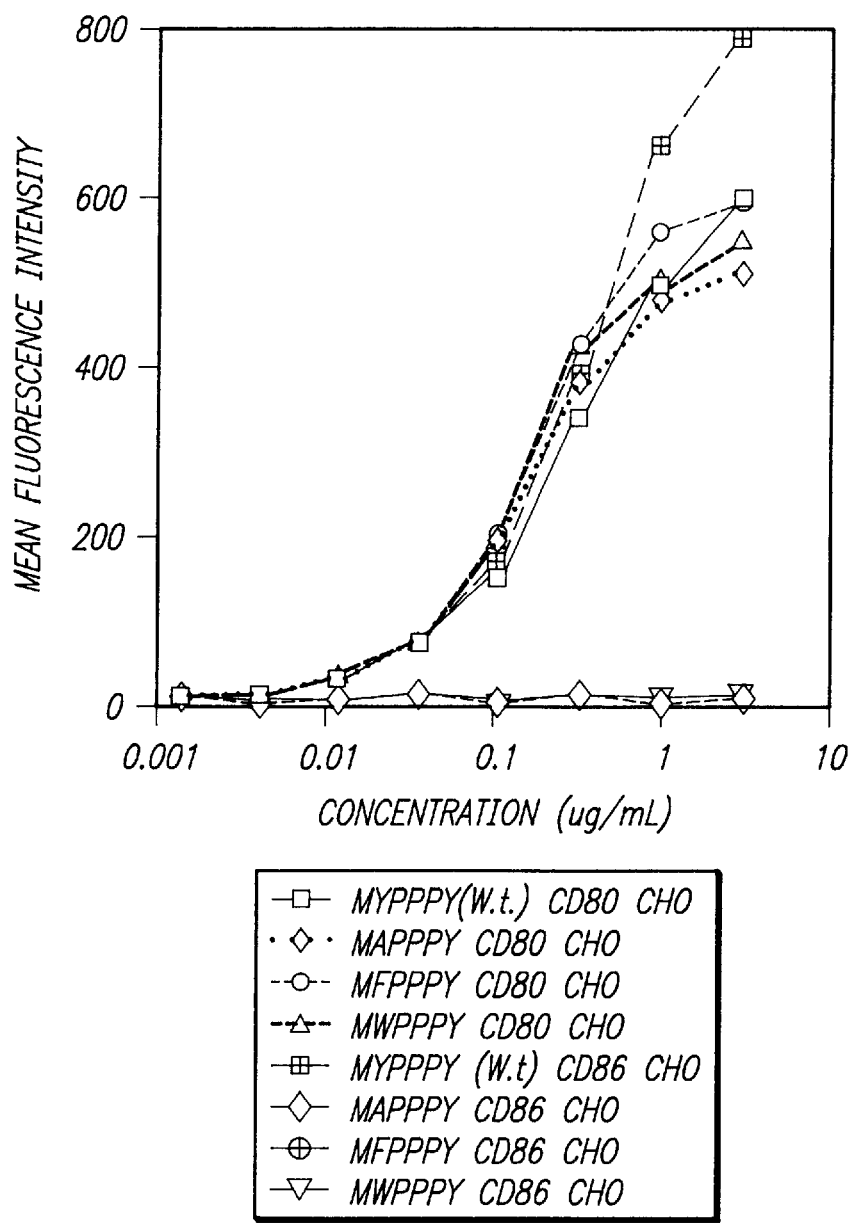

FIG. 8 further illustrates the unique characteristics of the two mutant molecules in which the first tyrosine in the MYPPPY (SEQ ID NO 11) motif has been replaced with either phenylalanine or tryptophan. FACS analysis over a range of different concentrations shows that these two mutants bind CD80 in a manner analogous to the wild type molecule but are completely unable to bind to CD86.

Figure 9:
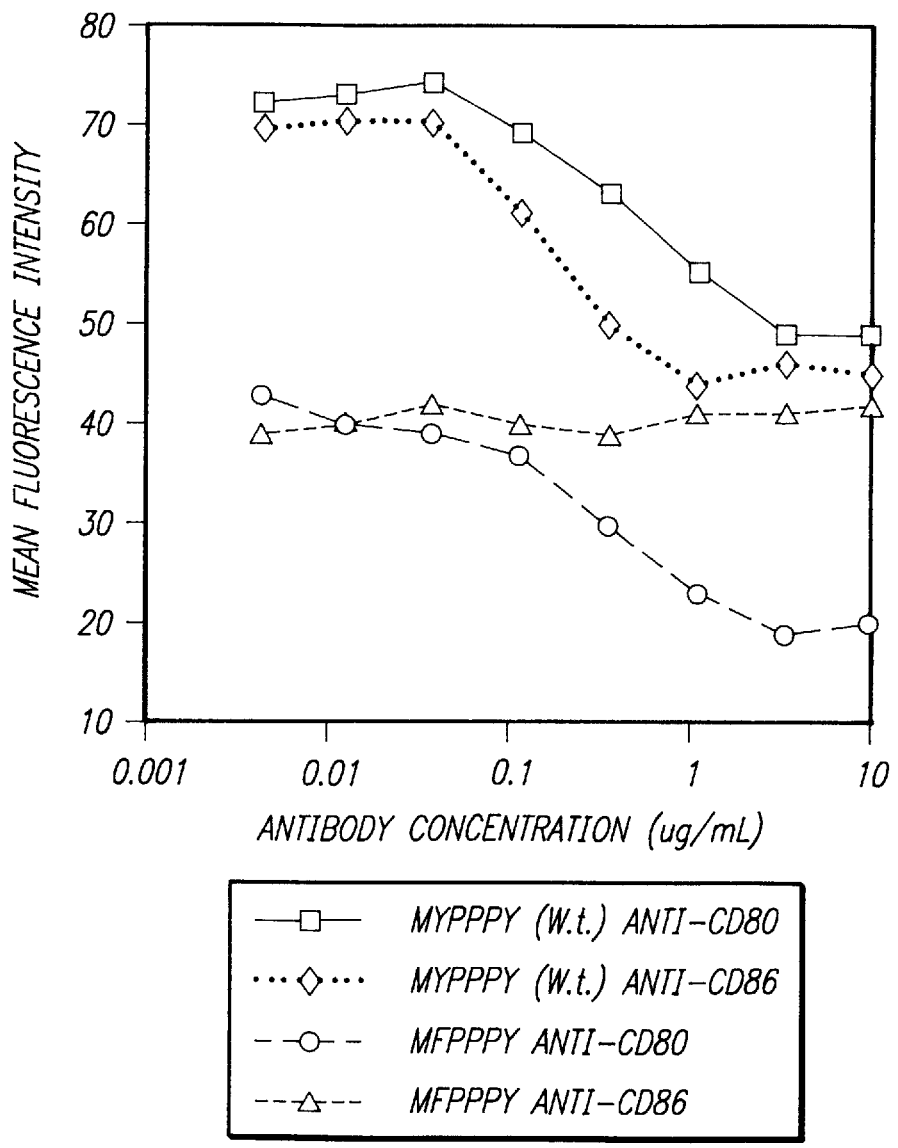

These observations are consistent with studies involving cell lines which naturally express the CD80 and CD86 antigens. FIG. 9 shows that the phenylalanine mutant binds to endogenous CD80 which is expressed on the surface of the cell line LCL 816. This mutant's specificity for the CD80 molecule is demonstrated in competition studies where its binding is inhibited by monoclonal antibodies which are specific for CD80. Further, antibodies specific for CD86 have no effect on this molecule's ability to bind to this cell line.

This data clearly demonstrates that the first tyrosine in the MYPPPY motif in CTLA4Ig plays a critical role in this molecule's ability to bind both CD80 and CD86. In addition, these results show that substitutions which change the residue at this position to either a phenylalanine or a tryptophan generate mutants which retain the ability to bind CD80 but lose the ability to bind CD86.

TABLE I

CTLA4/CD28Ig homolog mutant junction sequences.

| MUTANT | | | | | | | |
|---|---|---|---|---|---|---|---|
| HS1 | -22CKYasp27- | | | | -93ckvEVM99- | | -123CPSDQE- |
| HS2 | -20fvcKYS25- | | | | -94CKIelm98- | | -121cpdDQE- |
| HS3 | | | | | -93ckvEVM99- | | -123CPSDQE- |
| HS4 | | | | | -94CKIelm98- | | -121cpdDQE- |
| HS5 | -22CKYasp27- | -30ateFRA35- | | | | | -123CPSDQE- |
| HS6 | -22ceySYN27- | -30SREvrv35- | | | | | -121cpdDQE- |
| HS4-A | | | | | -94CKIelm98- | -111tqiHVK118- | -123CPSDQE- |
| RS4-B | | | | | | -113TIIyvi116- | -121cpdDQE- |
| RS7 | -22CKYasp27- | -30ateFRA35- | | | -94CKIelm98- | | -121cpdDQE- |
| R58 | -22CKYasp27- | -30ateFRA35- | | | -94CKIelm98- | -111tqiHVK118- | -123CPSDQE- |
| HS9 | -22CKYasp27- | -30ateFRA35- | | | | -113TIIyvi116- | -121cpdDQE- |
| HS10 | | | -47VCVaty53- | -56gneLQV60- | -94CKIelm98- | | -121cpdDQE- |
| HS11 | -22CKYasp27- | -30ateFRA35- | -47VCVaty53- | -56gneLQV60- | -94CKIelm98- | | -121cpdDQE- |
| HS12 | | | -47VCVaty53- | -56gneLQV60- | -94CKLelm98- | -111tqiHVK118- | -123CPSDQE- |
| HS13 | -22CKYasp27- | -30ateFRA35- | -47VCVaty53- | -56gneLQV60- | -94CKIelm98- | -111tqiHVK118- | -123CPSDQE- |
| HS14 | | | -47VCVaty53- | -56gneLQV60- | | | -123CPSDQE- |

Junction sequences of the CTLA4/CD28-Ig hybrid fusion proteins. Amino acids are denoted by their single letter code with those in upper case being CD28 residues, those in lower case being CTLA4 residues and those in bold upper case being human IgG1 residues. Numbering in the table is from the N-terminal methionine of the respective proteins and refers to the adjacent amino acids.

TABLE II

Binding of CTLA4 and CD28 monoclonal antibodies to CTLA4Ig and CD28Ig mutant fusion proteins and to CTLA4/CD28Ig hybrid fusion proteins.

| | anti-CTLA4 mAbs | | | anti-CD28 mAb |
|---|---|---|---|---|
| | 7F8 | 11D4 | 10A8 | 9.3 |
| CTLA4Ig MUTANT FUSION PROTEIN | | | | |
| AYPPPY | +++ | +++ | +++ | − |
| MAPPPY | ++ | + | ++ | − |
| MYAPPY | + | − | + | − |
| MYPAPY | +++ | +++ | +++ | − |
| MYPPAY | +++ | − | + | − |
| MYPPPA | +++ | ++ | +++ | − |
| AAPPPY | + | ++ | +++ | − |
| CD28Ig MUTANT FUSION PROTEIN | | | | |
| MYPPAY | − | − | − | − |
| MYPPPA | − | − | − | + |
| CTLA4/CD28Ig HYBRID FUSION PROTEINS | | | | |
| HS1 | − | − | − | − |
| HS2 | − | − | − | + |
| HS3 | − | − | − | − |
| HS4 | − | − | − | +++ |
| HS5 | − | − | − | − |
| HS6 | + | − | − | − |
| HS4-A | − | − | − | ++ |
| HS4-B | − | − | − | ++ |
| HS7 | − | − | − | +++ |
| HS8 | − | + | − | +++ |
| HS9 | − | + | − | − |
| HS10 | − | − | − | − |
| HS11 | − | − | − | + |
| HS12 | − | − | − | − |
| HS13 | − | − | − | − |
| HS14 | − | − | − | − |
| CTLA4Ig | +++ | +++ | +++ | − |
| CD28Ig | − | − | − | +++ |

Antibody binding was rated from that seen for wild type protein (+++) to above background (+), and no detectable binding (−).

---

What is claimed is:

1. A CTLA4 mutant molecule reactive with the CD80 antigen, wherein in the extracellular domain of CTLA4 the first tyrosine in the amino acid motif MYPPPY (SEQ ID NO 11) is replaced by an amino acid other than tyrosine.

2. The CTLA4 mutant molecule of claim 1, wherein the amino acid replacing the first tyrosine is alanine, arginine, asparagine, aspartic acid, cysteine, glutamine, glutamic acid, glycine, histidine, isoleucine, leucine, lysine, methionine, phenylalanine, proline, serine, threonine, tryptophan, or valine.

3. The CTLA4 mutant molecule of claim 1, wherein the amino acid replacing the first tyrosine is phenylalanine.

4. The CTLA4 mutant molecule of claim 1, wherein the amino acid replacing the first tyrosine is tryptophan.

5. A soluble CTLA4 mutant molecule of claim 1 or 2.

6. The CTLA4 mutant molecules of claim 1 which binds the CD80 antigen but not the CD86 antigen.

7. The CTLA4 mutant molecule of claim 1 joined to a non-CTLA4 molecule.

8. The CTLA4 mutant molecule of claim 7, wherein the non-CTLA4 protein is at least a portion of an immunoglobulin molecule.

9. A CTLA4Ig mutant fusion molecule having a first amino acid sequence consisting of the extracellular domain of the CTLA4 mutant molecule of claim 1 and a second amino acid sequence comprising the hinge, CH2 and CH3 regions of an immunoglobulin.

10. A purified protein of claim 1 or 9.

11. A nucleic acid molecule encoding the protein of claim 10.

12. A DNA molecule of claim 11.

13. A cDNA molecule of claim 12.

14. A plasmid comprising the cDNA molecule of claim 13.

15. A host-vector system comprising the plasmid of claim 14 transfected into a compatible eucaryotic host cell.

16. The host-vector system of claim 15, wherein the compatible eucaryotic host cells are Chinese Hamster Ovary cells.

17. A method for producing a CTLA4 mutant molecule comprising growing the host vector system of claim 15 so as to produce the CTLA4 mutant molecule in the host and recovering the CTLA4 mutant molecule so produced.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 234 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:1:

```
Met Ala Cys Leu Gly Phe Gln Arg His Lys Ala Gln Leu Asn Leu Ala
 1               5                  10                  15
Ala Arg Thr Trp Pro Cys Thr Leu Leu Phe Phe Leu Leu Phe Ile Pro
                20                  25                  30
Val Phe Cys Lys Ala Met His Val Ala Gln Pro Ala Val Val Leu Ala
                35                  40                  45
Ser Ser Arg Gly Ile Ala Ser Phe Val Cys Glu Tyr Ala Ser Pro Gly
        50                  55                  60
Lys Ala Thr Glu Val Arg Val Thr Val Leu Arg Gln Ala Asp Ser Gln
65                  70                  75                  80
```

```
Val  Thr  Glu  Val  Cys  Ala  Ala  Thr  Tyr  Met  Thr  Gly  Asn  Glu  Leu  Thr
               85                      90                       95

Phe  Leu  Asp  Asp  Ser  Xaa  Xaa  Ile  Cys  Thr  Gly  Thr  Ser  Ser  Gly  Asn
               100                     105                      110

Gln  Val  Asn  Leu  Thr  Ile  Gln  Gly  Leu  Arg  Ala  Met  Asp  Thr  Gly  Leu
               115                     120                      125

Tyr  Ile  Cys  Lys  Val  Glu  Leu  Met  Tyr  Pro  Pro  Pro  Tyr  Tyr  Leu  Xaa
     130                      135                     140

Gly  Ile  Gly  Asn  Gly  Thr  Gln  Ile  Tyr  Val  Ile  Asp  Pro  Glu  Pro  Cys
145                      150                     155                      160

Xaa  Xaa  Xaa  Xaa  Xaa  Pro  Asp  Ser  Asp  Phe  Leu  Leu  Trp  Ile  Leu  Ala
               165                     170                      175

Ala  Val  Ser  Ser  Gly  Leu  Phe  Phe  Tyr  Ser  Phe  Leu  Leu  Thr  Xaa  Ala
               180                     185                      190

Val  Ser  Leu  Ser  Lys  Met  Leu  Lys  Lys  Arg  Ser  Pro  Leu  Thr  Thr  Gly
          195                      200                     205

Val  Tyr  Val  Lys  Met  Pro  Pro  Thr  Glu  Pro  Glu  Cys  Glu  Xaa  Xaa  Lys
     210                      215                     220

Gln  Phe  Gln  Pro  Tyr  Phe  Ile  Pro  Ile  Asn
225                      230
```

( 2 ) INFORMATION FOR SEQ ID NO:2:

( i ) SEQUENCE CHARACTERISTICS:
        ( A ) LENGTH: 234 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:2:

```
Met  Ala  Cys  Leu  Gly  Leu  Arg  Arg  Tyr  Lys  Ala  Gln  Leu  Gln  Leu  Pro
1                   5                      10                       15

Ser  Arg  Thr  Trp  Pro  Phe  Val  Ala  Leu  Leu  Thr  Leu  Leu  Phe  Ile  Pro
               20                      25                       30

Val  Phe  Ser  Glu  Ala  Ile  Gln  Val  Thr  Gln  Pro  Ser  Val  Tyr  Leu  Ala
          35                      40                      45

Ser  Ser  His  Gly  Tyr  Ala  Ser  Phe  Pro  Cys  Glu  Tyr  Ser  Pro  Ser  His
     50                      55                      60

Asn  Thr  Asp  Glu  Tyr  Arg  Val  Thr  Val  Leu  Arg  Gln  Thr  Asn  Asp  Gln
65                       70                      75                       80

Met  Thr  Glu  Val  Cys  Ala  Thr  Thr  Phe  Thr  Glu  Lys  Asn  Thr  Val  Gly
               85                      90                       95

Phe  Leu  Asp  Tyr  Pro  Xaa  Xaa  Phe  Cys  Ser  Gly  Thr  Phe  Asn  Glu  Ser
               100                     105                      110

Arg  Val  Asn  Leu  Thr  Ile  Gln  Gly  Leu  Arg  Ala  Val  Asp  Thr  Gly  Leu
               115                     120                      125

Tyr  Leu  Cys  Lys  Val  Glu  Leu  Met  Tyr  Pro  Pro  Pro  Tyr  Phe  Val  Xaa
     130                      135                     140

Gly  Met  Gly  Asn  Gly  Thr  Gln  Ile  Tyr  Tyr  Ile  Asp  Pro  Glu  Pro  Cys
145                      150                     155                      160

Xaa  Xaa  Xaa  Xaa  Xaa  Pro  Asp  Ser  Asp  Phe  Leu  Leu  Trp  Ile  Leu  Tyr
               165                     170                      175

Ala  Val  Ser  Leu  Gly  Leu  Phe  Phe  Tyr  Ser  Phe  Leu  Val  Ser  Xaa  Ala
               180                     185                      190
```

```
Val  Ser  Leu  Ser  Lys  Met  Leu  Lys  Lys  Arg  Ser  Pro  Leu  Thr  Thr  Gly
          195                200                     205

Val  Tyr  Val  Lys  Met  Pro  Pro  Thr  Glu  Pro  Glu  Cys  Glu  Xaa  Xaa  Lys
     210                215                          220

Gln  Phe  Gln  Pro  Tyr  Phe  Ile  Pro  Ile  Asn
225                 230
```

( 2 ) INFORMATION FOR SEQ ID NO:3:

( i ) SEQUENCE CHARACTERISTICS:
      ( A ) LENGTH: 225 amino acids
      ( B ) TYPE: amino acid
      ( C ) STRANDEDNESS:
      ( D ) TOPOLOGY: linear ( i i ) MOLECULE TYPE: protein ( x i ) SEQUENCE DESCRIPTION: SEQ ID NO:3:

```
Met  Thr  Leu  Arg  Leu  Leu  Phe  Leu  Ala  Leu  Asn  Phe  Phe  Xaa  Ser  Val
1               5                    10                        15

Gln  Val  Thr  Glu  Asn  Lys  Ile  Leu  Val  Lys  Gln  Ser  Pro  Leu  Leu  Tyr
          20                    25                       30

Val  Asp  Ser  Asn  Glu  Val  Xaa  Ser  Leu  Ser  Cys  Arg  Tyr  Ser  Tyr  Asn
               35                40                      45

Leu  Leu  Ala  Lys  Glu  Phe  Arg  Ala  Ser  Leu  Tyr  Lys  Gly  Val  Asn  Ser
          50                    55                       60

Asp  Val  Xaa  Glu  Val  Cys  Val  Gly  Asn  Gly  Asn  Phe  Thr  Tyr  Gln  Pro
65                       70                    75                        80

Gln  Phe  Arg  Ser  Asn  Ala  Glu  Phe  Asn  Cys  Asp  Gly  Asp  Phe  Asp  Asn
               85                    90                        95

Glu  Thr  Val  Thr  Phe  Arg  Leu  Trp  Asn  Leu  His  Val  Asn  His  Thr  Asp
               100                   105                  110

Ile  Tyr  Phe  Cys  Lys  Ile  Glu  Phe  Met  Tyr  Pro  Pro  Pro  Tyr  Leu  Asp
          115                     120                  125

Asn  Glu  Arg  Ser  Asn  Gly  Thr  Ile  Ile  His  Ile  Lys  Glu  Lys  His  Leu
     130                      135                 140

Cys  His  Thr  Xaa  Xaa  Xaa  Gln  Ser  Ser  Pro  Lys  Leu  Phe  Trp  Ala  Leu
145                 150                      155                          160

Tyr  Val  Val  Ala  Gly  Val  Leu  Phe  Cys  Tyr  Gly  Leu  Leu  Val  Thr  Val
               165                     170                       175

Ala  Leu  Cys  Val  Ile  Trp  Thr  Asn  Ser  Arg  Arg  Asn  Arg  Leu  Leu  Gln
               180                  185                      190

Val  Thr  Tyr  Met  Asn  Met  Thr  Pro  Arg  Arg  Pro  Gly  Leu  Thr  Arg  Xaa
          195                200                      205

Lys  Pro  Tyr  Gln  Pro  Tyr  Ala  Pro  Ala  Arg  Asp  Phe  Ala  Ala  Tyr  Arg
     210                215                          220

Pro

225
```

( 2 ) INFORMATION FOR SEQ ID NO:4:

( i ) SEQUENCE CHARACTERISTICS:
      ( A ) LENGTH: 225 amino acids
      ( B ) TYPE: amino acid
      ( C ) STRANDEDNESS:
      ( D ) TOPOLOGY: linear ( i i ) MOLECULE TYPE: protein ( x i ) SEQUENCE DESCRIPTION: SEQ ID NO:4:

```
Met Thr Leu Arg Leu Leu Phe Leu Ala Leu Ser Phe Phe Xaa Ser Val
1               5                   10                  15

Gln Val Thr Glu Asn Lys Ile Leu Val Lys Gln Ser Pro Leu Leu Val
            20                  25                  30

Tyr Asp Asn Asn Glu Val Xaa Ser Leu Ser Cys Arg Tyr Ser Tyr Asn
        35                  40                  45

Leu Leu Ala Lys Glu Phe Arg Ala Ser Leu Tyr Lys Gly Val Asn Ser
    50                  55                  60

Asp Val Xaa Glu Val Cys Val Gly Asn Gly Asn Phe Thr Tyr Gln Pro
65                      70                  75                  80

Gln Phe Arg Pro Asn Val Gly Phe Asn Cys Asp Gly Asn Phe Asp Asn
                85                  90                      95

Glu Thr Val Thr Phe Arg Leu Trp Asn Leu Asp Val Asn His Thr Asp
            100                 105                 110

Ile Tyr Phe Cys Lys Ile Glu Val Met Tyr Pro Pro Pro Tyr Leu Asp
        115                 120                 125

Asn Glu Lys Ser Asn Gly Thr Ile Ile His Ile Lys Glu Lys His Leu
    130                 135                 140

Cys His Ala Xaa Xaa Xaa Gln Thr Ser Pro Lys Leu Phe Trp Pro Leu
145                 150                 155                 160

Val Val Val Ala Gly Val Leu Leu Cys Tyr Gly Leu Leu Tyr Thr Val
                165                 170                 175

Thr Leu Cys Ile Ile Trp Thr Asn Ser Arg Arg Asn Arg Leu Leu Gln
        180                 185                 190

Ser Asp Tyr Met Asn Met Thr Pro Arg Arg Leu Gly Pro Thr Arg Xaa
        195                 200                 205

Lys His Tyr Gln Pro Tyr Ala Pro Ala Arg Asp Phe Ala Ala Tyr Arg
    210                 215                 220

Pro
225
```

( 2 ) INFORMATION FOR SEQ ID NO:5:

( i ) SEQUENCE CHARACTERISTICS:
        ( A ) LENGTH: 223 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:5:

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Tyr Xaa Asn Leu Ser Cys Lys Tyr Ser Tyr Asn Leu Phe
        35                  40                  45

Ser Arg Glu Phe Arg Ala Ser Leu His Lys Gly Leu Asp Ser Ala Val
    50                  55                  60

Xaa Glu Val Cys Val Val Tyr Gly Asn Tyr Ser Gln Gln Leu Gln Val
65                  70                  75                  80

Tyr Ser Lys Thr Gly Phe Asn Cys Asp Gly Lys Leu Gly Asn Glu Ser
            85                  90                  95

Val Thr Phe Tyr Leu Gln Asn Leu Tyr Val Asn Gln Thr Asp Ile Tyr
        100                 105                 110
```

```
Phe Cys Lys Ile Glu Val Met Tyr Pro Pro Pro Tyr Leu Asp Asn Glu
        115             120             125
Lys Ser Asn Gly Thr Ile Ile His Val Lys Gly Lys His Leu Cys Pro
    130             135             140
Ser Pro Leu Phe Pro Gly Pro Ser Lys Pro Phe Trp Val Leu Val Val
145             150             155                         160
Val Gly Gly Val Leu Ala Cys Tyr Ser Leu Leu Tyr Thr Val Ala Phe
                165             170             175
Ile Ile Phe Trp Val Arg Ser Lys Arg Ser Arg Leu Leu His Ser Asp
            180             185             190
Tyr Met Asn Met Thr Pro Arg Arg Pro Gly Pro Thr Arg Xaa Lys His
        195             200             205
Tyr Gln Pro Tyr Ala Pro Pro Arg Asp Phe Ala Ala Tyr Arg Ser
    210             215             220
```

(2) INFORMATION FOR SEQ ID NO:6:

(i) SEQUENCE CHARACTERISTICS:
        (A) LENGTH: 226 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Leu Gly Ile Leu Val Val Leu Cys Leu Ile Pro Ala Ala Asp Val
1               5               10              15
Thr Glu Asn Lys Ile Leu Val Ala Gln Arg Pro Leu Leu Ile Val Ala
            20              25              30
Asn Arg Thr Ala Xaa Thr Leu Val Cys Asn Tyr Thr Tyr Asn Gly Thr
        35              40              45
Gly Lys Glu Phe Arg Ala Ser Leu His Lys Gly Thr Asp Ser Ala Val
    50              55              60
Xaa Glu Val Cys Phe Ile Ser Trp Asn Met Thr Xaa Lys Ile Asn Ser
65              70              75              80
Asn Ser Asn Lys Glu Phe Asn Cys Arg Gly Ile His Asp Lys Asp Lys
            85              90              95
Val Ile Phe Asn Leu Trp Asn Met Ser Ala Ser Gln Thr Asp Ile Tyr
        100             105             110
Phe Cys Lys Ile Glu Ala Met Tyr Pro Pro Pro Tyr Val Tyr Asn Glu
        115             120             125
Lys Ser Asn Gly Thr Val Ile His Tyr Arg Glu Thr Pro Ile Xaa Xaa
    130             135             140
Gln Thr Gln Glu Pro Glu Ser Ala Thr Ser Tyr Trp Val Met Tyr Ala
145             150             155                         160
Val Thr Gly Leu Leu Gly Phe Tyr Ser Met Leu Ile Thr Ala Val Phe
                165             170             175
Ile Ile Tyr Arg Gln Lys Ser Lys Arg Asn Arg Tyr Arg Gln Ser Asp
            180             185             190
Tyr Met Asn Met Thr Pro Arg His Pro Pro His Gln Lys Asn Lys Gly
        195             200             205
Tyr Pro Ser Tyr Ala Pro Thr Arg Asp Tyr Thr Ala Tyr Arg Ser Trp
    210             215             220
Gln Pro
225
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

Met Tyr Pro Pro Ala Tyr
1               5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

Met Tyr Pro Pro Pro Ala
1               5

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AATACGACTC ACTATAGG                                                                       18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CACCACACTG TATTAACC                                                                       18

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

Met Tyr Pro Pro Pro Tyr
1               5

( 2 ) INFORMATION FOR SEQ ID NO:12:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

TGCAAGGTGG AGCTCATGTT CCCACCGCCA TAC 33

( 2 ) INFORMATION FOR SEQ ID NO:13:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

GCGCTCGACT CTAGAAGCAT CCTCGTG 27